US012594438B2

(12) United States Patent
Warnking et al.

(10) Patent No.: US 12,594,438 B2
(45) Date of Patent: *Apr. 7, 2026

(54) BRONCHIAL DENERVATION USING INTEGRATED A-MODE SIGNAL FOR OPTIMIZATION OF ULTRASOUND TREATMENT

(71) Applicant: AerWave Medical, Inc., Naples, FL (US)

(72) Inventors: Reinhard J. Warnking, Westlake, FL (US); Satoshi Nishiaoki, Setauket, NY (US)

(73) Assignee: AerWave Medical, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/389,933

(22) Filed: Dec. 20, 2023

(65) Prior Publication Data

US 2024/0123262 A1      Apr. 18, 2024

Related U.S. Application Data

(63) Continuation of application No. 17/418,545, filed as application No. PCT/US2021/015825 on Jan. 29, 2021, now abandoned.

(Continued)

(51) Int. Cl.
*A61N 7/00*       (2006.01)
*A61B 8/00*       (2006.01)
(Continued)

(52) U.S. Cl.
CPC ................ *A61N 7/00* (2013.01); *A61B 8/085* (2013.01); *A61B 8/12* (2013.01); *A61B 8/429* (2013.01);
(Continued)

(58) Field of Classification Search
None
See application file for complete search history.

(56) References Cited

U.S. PATENT DOCUMENTS 6,984,993 B2    1/2006   Ariav
8,425,455 B2    4/2013   Nentwick
(Continued)

FOREIGN PATENT DOCUMENTS

EP       1159036      6/2007
EP       2521593     12/2015
(Continued)

OTHER PUBLICATIONS

Armitage, L., & Rachel, B. (Jun. 22, 2020). Inhaled corticosteroids: A rapid review of the evidence for treatment or prevention of COVID-19. Retrieved Aug. 20, 2020, from https://www.cebm.net/covid-19/inhaled-corticosteroids-a-rapid-review-of-the-evidence-for-treatment-or-prevention-of-covid-19/ (Year: 2020).

(Continued)

*Primary Examiner* — Angela M Hoffa
(74) *Attorney, Agent, or Firm* — Neil D. Gershon

(57) ABSTRACT

Apparatus and methods for deactivating bronchial nerves extending along a bronchial branch of a mammalian subject to treat asthma and related conditions. An ultrasonic transducer (11) is inserted into the bronchus as, for example, by advancing the distal end of a catheter (10) bearing the transducer into the bronchial section to be treated. The ultrasonic transducer emits focused ultrasound so as to heat tissues throughout circular impact volume (13) as, for example, at least about 1 cm³ encompassing the bronchus to a temperature sufficient to inactivate nerve conduction but insufficient to cause rapid ablation or necrosis of the tissues. The treatment can be performed without locating or focusing on individual bronchial nerves.

18 Claims, 14 Drawing Sheets

Related U.S. Application Data

(60) Provisional application No. 63/002,555, filed on Mar. 31, 2020.

(51) Int. Cl.

| | |
|---|---|
| *A61B 8/08* | (2006.01) |
| *A61B 8/12* | (2006.01) |
| *A61N 7/02* | (2006.01) |
| *A61B 1/00* | (2006.01) |

(52) U.S. Cl.
CPC .......... *A61N 7/022* (2013.01); *A61B 1/00082* (2013.01); *A61N 2007/0004* (2013.01); *A61N 2007/003* (2013.01); *A61N 2007/0043* (2013.01); *A61N 2007/0052* (2013.01); *A61N 2007/0082* (2013.01)

(56)  References Cited

U.S. PATENT DOCUMENTS

| | | | |
|---|---|---|---|
| 8,992,447 | B2 | 3/2015 | Gertner |
| 10,828,462 | B2 | 11/2020 | Daniels et al. |
| 11,020,618 | B1 | 6/2021 | Warnking |
| 11,273,330 | B2 | 3/2022 | Warnking |
| 11,278,313 | B2 | 3/2022 | Warnking |
| 11,446,524 | B2 | 9/2022 | Mayse et al. |
| 11,565,135 | B2 * | 1/2023 | Warnking .............. A61N 7/022 |
| 11,607,568 | B2 * | 3/2023 | Warnking ................ A61B 8/12 |
| 2003/0060813 | A1 | 3/2003 | Loeb |
| 2003/0078645 | A1 | 4/2003 | Pigott |
| 2003/0191392 | A1 | 10/2003 | Haldeman |
| 2005/0222558 | A1 | 10/2005 | Baxter |
| 2008/0287837 | A1 | 11/2008 | Makin |
| 2011/0144491 | A1 | 6/2011 | Sliwa |
| 2011/0245665 | A1 | 10/2011 | Nentwick |
| 2011/0257523 | A1 | 10/2011 | Hastings et al. |
| 2011/0257561 | A1 | 10/2011 | Gertner |
| 2012/0143099 | A1 | 6/2012 | Daniels et al. |
| 2013/0103028 | A1 | 4/2013 | Tsoref |
| 2013/0197555 | A1 | 8/2013 | Schaer et al. |
| 2013/0281889 | A1 | 10/2013 | Gertner |
| 2014/0031727 | A1 | 1/2014 | Warnking |
| 2016/0008636 | A1 | 1/2016 | Warnking |
| 2016/0113699 | A1 | 4/2016 | Sverdlik |
| 2016/0220851 | A1 | 8/2016 | Mayse |
| 2016/0287912 | A1 * | 10/2016 | Warnking ............ A61B 8/5207 |
| 2017/0014159 | A1 | 1/2017 | Stokes |
| 2018/0146839 | A1 | 5/2018 | Friedlander et al. |
| 2020/0238085 | A1 | 7/2020 | Khodaparast |
| 2020/0246069 | A1 | 8/2020 | Rioux et al. |
| 2021/0316161 | A1 | 10/2021 | Warnking et al. |
| 2022/0008753 | A1 | 1/2022 | Warnking et al. |
| 2023/0009916 | A1 * | 1/2023 | Mayse ................... A61N 7/022 |
| 2024/0366967 | A1 * | 11/2024 | Warnking .............. A61B 8/085 |

FOREIGN PATENT DOCUMENTS

| | | |
|---|---|---|
| WO | WO 2007/009118 | 1/2007 |
| WO | WO 2011/053757 | 5/2011 |
| WO | WO 2012/120495 | 9/2012 |
| WO | WO 2013/048912 | 4/2013 |
| WO | WO 2014/022777 | 2/2014 |
| WO | WO 2015/066424 | 5/2015 |
| WO | WO 2021/201963 | 10/2021 |

OTHER PUBLICATIONS

Buehler, Markus J. "Nanomechanical sonification of the 2019-nCoV coronavirus spike protein through a materiomusical approach." Apr. 2, 2020, https://web.archive.org/web/20200402064158/hllps://arxiv.org/ftp/arxiv/papers/2003/2003.14258.pdf. Accessed Apr. 2, 2021. (Year: 2020).

M. C. (Apr. 24, 2020). Turning up the heat on COVID-19: Heat as a therapeutic intervention. Retrieved Aug. 20, 2020, from https://f1 000research .com/articles/9-292/v1 (Year: 2020).

Marcela, M. (May 18, 2020). The Use of Core Warming as a Treatment for Coronavirus Disease 2019 (COVID-19): An Initial Mathematical Model. Retrieved Aug. 20, 2020, from https://jca.emnuvens.com.br/jca/article/view/3382/3396 (Year: 2020).

Nuvaira. "Minimally Invasive Procedure for COPD Treatment." Nuvaira, Dec. 26, 2019, web.archive.org/web/20191226085420/www.nuvaira.com/the-procedure/. Accessed Apr. 2, 2021. (Year: 2019).

Q&A: Dexamethasone and COVID-19. (Jun. 25, 2020). Retrieved Aug. 20, 2020, from https://www.who.int/news-room/q-a-detail/q-a-dexamethasone-and-covid-19 (Year: 2020).

Xu, Z., et al. (Feb. 18, 2020). Pathological findings of COVID-19 associated with acute respiratory distress syndrome. Retrieved Aug. 20, 2020, from https://www.sciencedirect.com/science/article/pii/S221326002030076X?via=ihub (Year: 2020).

Zurn, R. (May 28, 2020). Ultrasound may prove to be effective, noninvasive treatment for COVID-19. Retrieved Aug. 20, 2020, from https://cse.umn.edu/college/feature-stories/ultrasound-may-prove-be-effective-noninvasive-treatment-covid-19 (Year: 2020).

PCT/US2021/015825 International Search Report dated Apr. 29, 2021.

EP 21779200 Search Report dated Mar. 27, 2024.

PCT/US2023/034610 International Search Report dated Mar. 13, 2024.

PCT/US2023/034606 International Search Report dated Apr. 19, 2024.

* cited by examiner

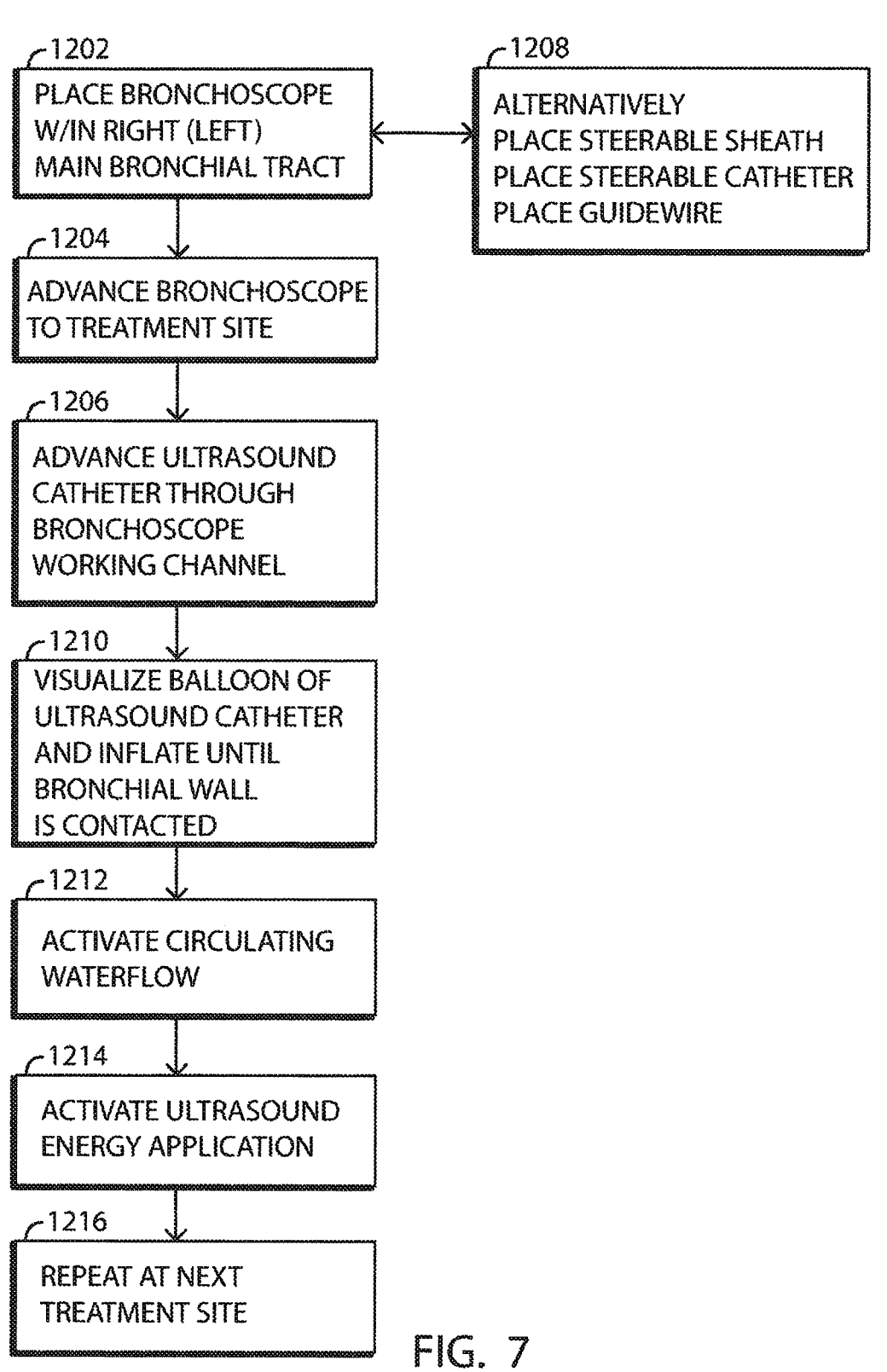

1202
PLACE BRONCHOSCOPE
W/IN RIGHT (LEFT)
MAIN BRONCHIAL TRACT

1208
ALTERNATIVELY
PLACE STEERABLE SHEATH
PLACE STEERABLE CATHETER
PLACE GUIDEWIRE

1204
ADVANCE BRONCHOSCOPE
TO TREATMENT SITE

1206
ADVANCE ULTRASOUND
CATHETER THROUGH
BRONCHOSCOPE
WORKING CHANNEL

1210
VISUALIZE BALLOON OF
ULTRASOUND CATHETER
AND INFLATE UNTIL
BRONCHIAL WALL
IS CONTACTED

1212
ACTIVATE CIRCULATING
WATERFLOW

1214
ACTIVATE ULTRASOUND
ENERGY APPLICATION

1216
REPEAT AT NEXT
TREATMENT SITE

FIG. 7

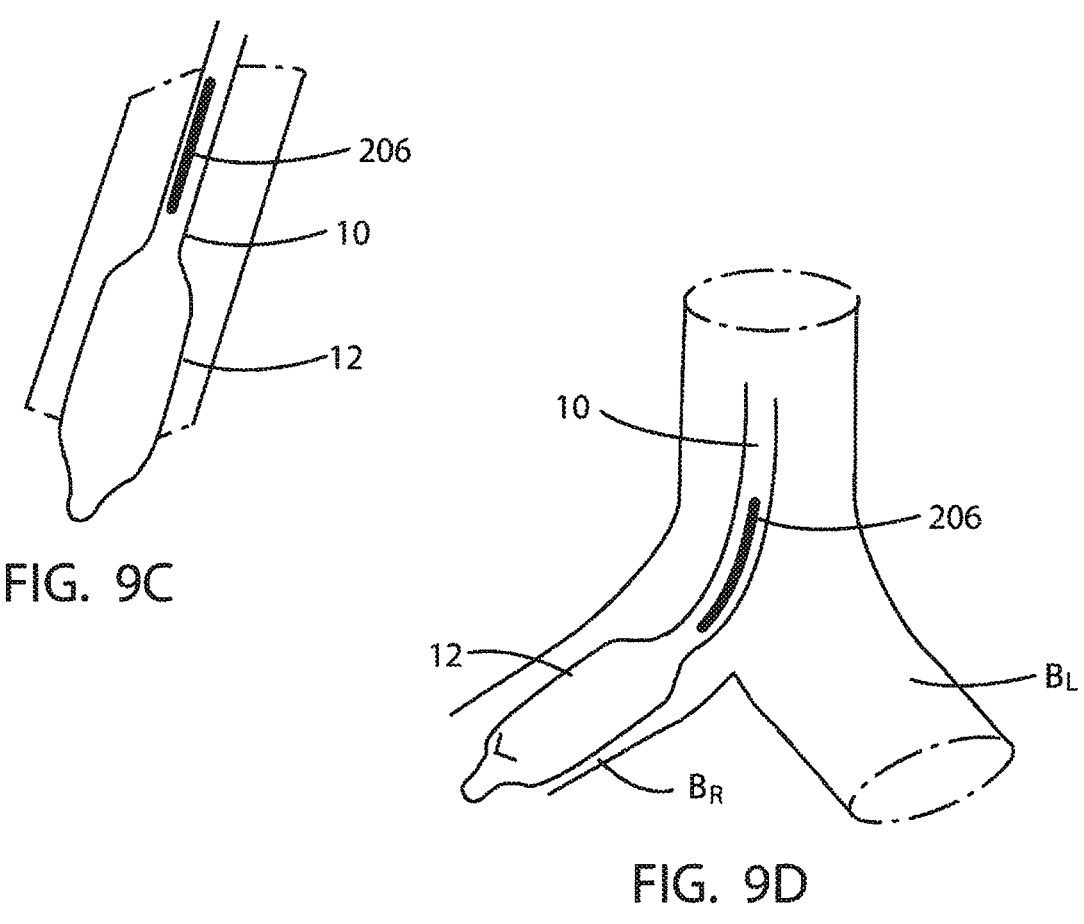
FIG. 9C
FIG. 9D
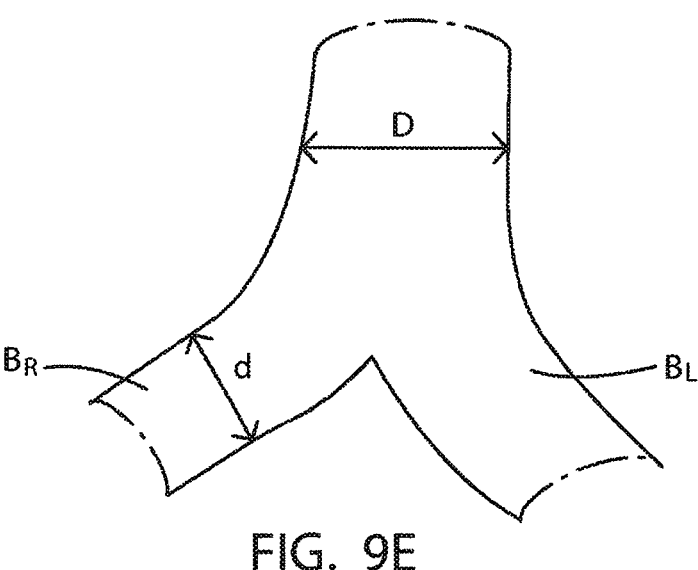
FIG. 9E

BRONCHIAL DENERVATION USING INTEGRATED A-MODE SIGNAL FOR OPTIMIZATION OF ULTRASOUND TREATMENT

This application is a continuation of application Ser. No. 17/418,545, filed Jun. 25, 2021, which is a 371 of PCT application serial no. PCT/US2021/015825, filed Jan. 29, 2021, which claims priority to provisional application Ser. No. 63/002,555, filed Mar. 31, 2020. The entire contents of each of these applications are incorporated herein by reference.

FIELD OF THE INVENTION

The invention relates to an apparatus and an associated method for the treatment of asthma and other pulmonary indications. The invention contemplates the use of a circumferential focused ultrasound field.

BACKGROUND OF THE INVENTION

Successful treatment of pulmonary diseases such as asthma and COPD is important since these diseases represent a significant global health issue with reduced quality of life. While drug therapy (Bronchodilators, Anti Inflammatories and Leukotrines Modifiers) can be used to treat asthma, it is not always successful and is very expensive. Asthma is a disorder characterized by airway constriction and inflammation resulting in breathing difficulties. Wheezing, shortness of breath and coughing are typical symptoms.

These symptoms are caused by increased mucus production, airway inflammation and smooth muscle contraction resulting in airway obstruction. This obstruction can be treated by injuring and scaring the bronchial walls. This remodeling of the bronchial walls stiffens the bronchia and reduces contractility. Mechanical means and heat application have been proposed as in U.S. Pat. No. 8,267,094. Other approaches focus on destruction of smooth muscle cells surrounding the bronchia as described in US Patent Application Publication No. 2012/0143099A1 and U.S. Pat. No. 7,906,124. Other techniques include applying RF energy to the bronchial wall and thereby directly widening the bronchia through a process which is not disclosed as in U.S. Pat. Nos. 7,740,017 and 8,161,978. Whatever the process, the bronchial wall will be damaged and the procedure therefore has to be staged as described in U.S. Pat. No. 7,740,017. European Patent No. 2405841 describes applications of heat shocks through infused agents.

Inactivating conduction of the nerves surrounding the bronchia has been proposed in US Patent Application Publication No. 2012/0203216 through mechanical action, i.e., puncturing, tearing, cutting nerve tissue. In US Patent Application Publication No. 2011/0000118 nerve tissue ablation occurs by applying energy (RF, HIFU, microwave, radiation and thermal energy) directly to the nerves percutaneously. It is not taught how to identify the nerve location in order to align the energy focal point (i.e. HIFU) with the nerve location. This is an issue since nerves are too small to be visualized with standard ultrasound, CT or MRI imaging methods. Therefore, the focal point of the energy field cannot be predictably aligned with the target or nerve location. U.S. Pat. No. 8,088,127 teaches to denervate by applying RF energy to the bronchial wall with the catheter positioned inside the bronchial lumen. It is proposed to protect the bronchial wall through simultaneous cooling of the wall. This is of course a very time intensive treatment approach since the RF ablation is limited to the electrode contact area. Therefore numerous ablation zones need to be pieced together to obtain a larger ablation zone with increased probability of affecting nerves. Efficacy might be severely limited due to the cooling action.

However, how to selectively target, predominantly nerves, without affecting the bronchial wall and surrounding tissue is not taught in the prior art. There is a need for a device and method to selectively ablate bronchial nerves without causing damage to bronchial walls and surrounding tissues. If this can be achieved, treatments would be much easier and faster to perform. Today's multiple treatments (see U.S. Pat. No. 7,740,017 and Alair System description, BSX) could be reduced to a one-time treatment, much better tolerated by patients and in particular COVID 19 patients. By selectively targeting nerves instead of tissue it is also likely that a more proximal single ablation of nerves (conducting signals to distal bronchial sections) will have the same clinical effect as treating the bronchial tree from proximal to distal with numerous energy applications.

In order to explain the difficulties associated with bronchial denervation without causing other damage, the anatomy of the bronchial system and nerves will be described now. Shown in FIG. 6 is an illustration of the bronchial tree. FIG. 3 shows a cross section of a bronchial tube surrounded with smooth muscle (7) and nerves (6). In addition, FIG. 5 shows a longitudinal section of a bronchus (BR) and the adjacent nerves (6). As can be seen from these two FIGS. 3 and 5), the bronchial nerves (6) surround the bronchial tubes. Different individuals have the nerves (6) in different circumferential locations around the bronchial tubes. In addition, the nerves may be at different radial distances from the central axis of the bronchial tube where the energy emitter (11) is placed (FIG. 3). It is not practical to locate the bronchial nerves by referring to anatomical landmarks. Moreover, it is difficult or impossible to locate individual bronchial nerves using conventional in vivo imaging technology. Furthermore, when denervation in the main bronchi is performed, cartilage rings will represent an obstacle in particular for ultrasound ablation. In US Patent Application Publication No. 2016 220851 mechanical means and overlapping ultrasound beams are proposed to seat the ultrasound source so ultrasound energy is applied between or behind cartilage rings. Except for the mechanical seating no apparatus or method is taught as to how to ensure optimal inter cartilage positioning. There is a need for a device and method to easily ensure energy source positioning between cartilage rings. It would be desirable to know whether the ultrasound treatment volume is actually deployed between cartilage rings or whether the ultrasound is reflected by cartilage rings. Also, enablement of complete circumferential ultrasound transmission with diameter dependent dose optimization is desirable.

The inability to locate and target the bronchial nerves (6) makes it difficult to interrupt or terminate the bronchial nerve activity using non-surgical techniques without causing damage to the bronchial walls or other side effects. For example, attempts to apply energy to the bronchial nerves can cause stenosis, and necrosis to the bronchi. In addition, the inability to target and locate the bronchial nerves (6) makes it difficult to ensure that bronchial nerve activity has been discontinued enough to achieve an acceptable therapeutic treatment.

U.S. Pat. No. 8,088,127 suggests the use of a radio frequency ("RF") emitter connected to a catheter, which is inserted in the bronchial tree. The RF emitter is placed against the bronchial wall and the RF energy is emitted to heat the nerves to a temperature that reduces the activity of bronchial nerves which happen to lie in the immediate vicinity of the emitter. In order to treat all the nerves surrounding the bronchial tubes, the RF emitter source must be repositioned around the inside of each bronchial tube section multiple times. In order to protect the bronchial wall this RF heat application is combined with a cooling application which makes the procedure even more complicated. The emitter may miss some of the bronchial nerves, leading to an incomplete treatment. Moreover, the RF energy source (electrode) must contact the bronchial wall to be able to heat the surrounding tissue and nerves, which may cause damage or necrosis to the inner lining of the bronchi.

The '118 patent also suggests the use of high-intensity focused ultrasound to deactivate the bronchial nerves. It is not clear how a High Intensity Focused Ultrasound (HIFU) zone can be aligned with the targeted bronchial nerves. It is difficult or impossible to align this highly focused zone with the bronchial nerves because it is difficult or impossible to visualize and target the bronchial nerves with current technology, and because the bronchial nerves may lie at different radial distances and circumferential locations from the central axis of bronchi. The latter problem is aggravated in patients who have bronchi with large variations in shape or thickness. Moreover, the focal point can encompass only a small segment of each bronchial nerve along the lengthwise direction of the bronchi. Since nerves tend to re-grow, a small treatment zone allows the nerves to reconnect in a shorter period of time.

For many years ultrasound has been used to enhance cell repair, stimulate the growth of bone cells, enhance delivery of drugs to specific tissues, and to image tissue within the body. In addition, high-intensity focused ultrasound has been used to heat and ablate tumors and tissue within the body. Ablation of tissue has been performed nearly exclusively by high-intensity focused ultrasound because the emitted ultrasound energy is focused on a specific location to allow precise in-depth tissue necrosis without affecting surrounding tissue and intervening structures that the ultrasound energy must pass through.

U.S. Pat. No. 6,117,101, to Diederich, discusses use of highly collimated ultrasound energy rather than high intensity focused ultrasound for ablating tissue to create a scar ring within the pulmonary vein for blocking the conduction of electrical signals to the heart (pulmonary vein isolation).

SUMMARY OF THE INVENTION

One aspect of the invention provides an apparatus for inactivating bronchial nerve conduction in a human or non-human mammalian subject. The apparatus according to this aspect of the invention preferably includes an ultrasound transducer adapted for insertion into the bronchial system of the mammalian subject. The ultrasound transducer desirably is arranged to transmit a ring of focused ultrasound energy (see FIGS. 8A-8C and 12). The apparatus according to this aspect of the invention desirably also includes an actuator which is electrically connected to the transducer. The actuator most preferably is adapted to control the ultrasound transducer to transmit focused ultrasound energy into an impact volume of at least approximately 1 cm³, encompassing the bronchial tube so that the circumferentially focused ultrasound energy is applied at a therapeutic level sufficient to inactivate conduction of bronchial nerves throughout the impact volume. This energy level is about ⅒ of the energy level typically applied for tissue necrosis. As discussed further below, such therapeutic level is below the level required for tissue ablation. By utilizing focused instead of unfocused ultrasound the safety margin is further increased, since the region where nerves are located, outside the bronchial tubes, is exposed to higher energy levels than the region of the bronchial wall through which the ultrasonic pressure waveform energy passes. Further the present invention contemplates use of a positioning sensor to ensure inter cartilage treatment.

The apparatus may further include a catheter with a distal end and a proximal end, the transducer being mounted to the catheter adjacent the distal end, the transducer being constructed and arranged inside a compliant balloon which will make contact with the bronchial wall. This compliant balloon is filled with a circulating cooling fluid to conduct ultrasound energy from the transducer to the bronchial walls and surrounding tissue and nerves. This cooling fluid also transports excessive heat away from the transducer. About half of the electrical energy supplied to the transducer is converted into heat while the other half is converted to ultrasonic energy. To be enabled for clinical use, the energy levels and balloon diameters must be adjusted in accordance with the diameter of the bronchus at the ablation site. If these parameters are not adjusted (i.e., if there is a constant energy setting for all bronchial diameters), there is a significant risk of either too much damage caused by the ultrasound ablation or not enough energy to properly ablate and denervate the lung. Therefore, in order to work with a range of bronchial diameters, the device must be enabled to adjust power settings of ultrasound based upon the diameter of the bronchial airway. Furthermore, if the balloon's expanded diameter is insufficiently large for the balloon to circumferentially contact the bronchus, the energy will not be delivered circumferentially into the bronchial wall and the denervation will be incomplete. Therefore, the device must also be enabled to detect whether circumferential balloon/bronchus contact is complete or partial.

The transducer may be configured to transmit the ultrasound energy in a 360° cylindrical pattern surrounding a longitudinal transducer axis, and the catheter may be constructed and arranged to hold the axis of the transducer generally parallel to the axis of the bronchial tube. Focusing mechanisms can be electronic as in a phased array or include a fluid lens 12' (FIG. 8B) or a mechanical lens 322 (FIG. 8C). In case of a fluid lens implemented by a suitable configured balloon 12' as shown in FIG. 8B, the diameter of the focal ring can be varied with balloon pressure by changing the shape of the compliant balloon 12' with pressure and therewith changing the lens effect. Of course the electronic focusing can also be adjusted based on the bronchial (i.e. balloon) diameter which can be calculated from balloon pressure as shown in FIG. 10A or through ultrasound pinging (see FIGS. 10B and 11).

Another alternative is a rotating single crystal or annular array transducer 11" (as shown in FIG. 12) as used in mechanical IVUS systems (i.e. BSX). Therapeutic ultrasound pulses and/or full rotations could be interleaved with imaging pulses to generate quasi simultaneous imaging/therapy modes. When an annular array transducer 11" as shown in FIG. 12 is utilized very high resolution images can be obtained. For denervation applications it is advisable to defocus the therapeutic annular array beam to a certain degree in order to avoid harmful energy densities in the focal zone and to ensure sufficiently large treatment volumes in order to maximize efficacy.

The system circulating the coupling/cooling fluid may measure the fluid volume and pressure and therewith determine the bronchial diameter, see FIG. 10A. Once the balloon is in circumferential contact with the bronchus, the system will detect a pressure increase without a significant volume increase which corresponds with a certain balloon/bronchial diameter. Based on this bronchial diameter the overall ultrasound power can be automatically optimized for different diameters.

A further aspect of the invention provides methods for inactivating bronchial nerve conduction in a mammalian subject. A method according to this aspect of the invention desirably includes the steps of inserting an ultrasound transducer into a bronchial branch of the subject and actuating the transducer to transmit therapeutically effective ultrasound energy into an circular impact volume of at least approximately 1 cm$^3$ encompassing the bronchial branch. The ultrasound energy desirably is applied so that the therapeutically effective ultrasound energy inactivates conduction of all the nerves in the impact volume. For example, the step of actuating the transducer may be so as to maintain the temperature of the bronchial wall below 65° C. while heating the solid tissues within the impact volume, including the nerves in the impact volume, to above 42° C.

Because the impact volume is relatively large, and because the tissues throughout the impact volume preferably reach temperatures sufficient to inactivate nerve conduction, the preferred methods according to this aspect of the invention can be performed successfully without determining the actual locations of the bronchial nerves, and without targeting or focusing on the bronchial nerves. The treatment can be performed without measuring the temperature of tissues. Moreover, the treatment preferably is performed without causing injury to the bronchi.

Further aspects of the invention provide probes which can be used in the method and apparatus discussed above, and apparatus incorporating means for performing the steps of the methods discussed above.

BRIEF DESCRIPTION OF THE DRAWINGS

FIG. 7 is a flow chart depicting steps in treating the bronchi pursuant to the present invention.

FIG. 9A through 9E are diagrams depicting respective catheter delivery methods without the use of a bronchoscope.

DETAILED DESCRIPTION

Figure 9A:
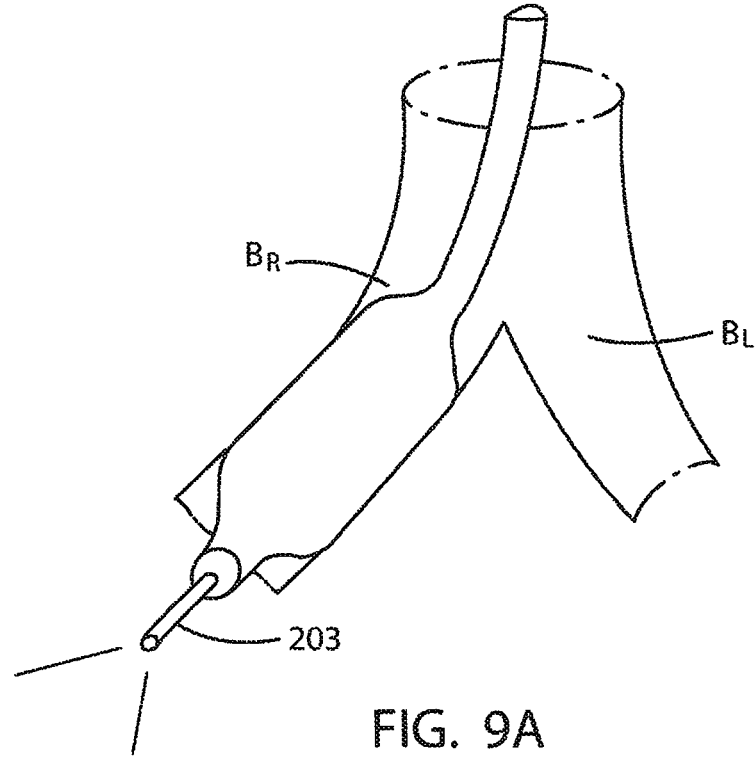
Figure 9B:
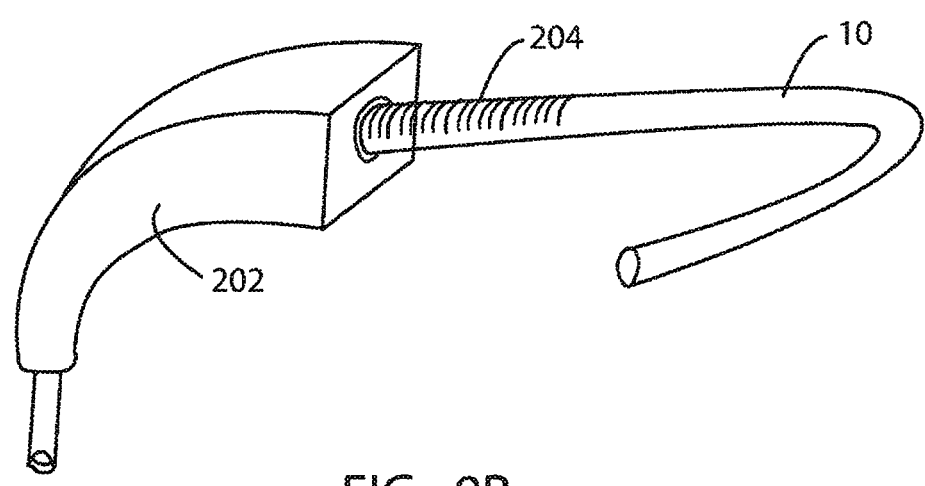
Figure 10B:
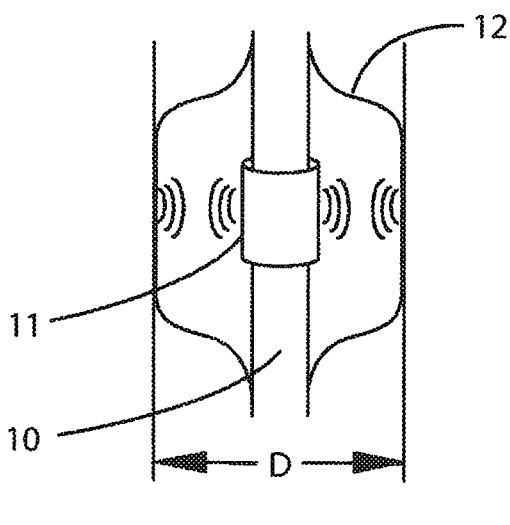
FIG. 10B is a schematic side elevational view of a device in accordance with the invention for use in determining bronchial diameters through ultrasound pinging.
Figure 11:
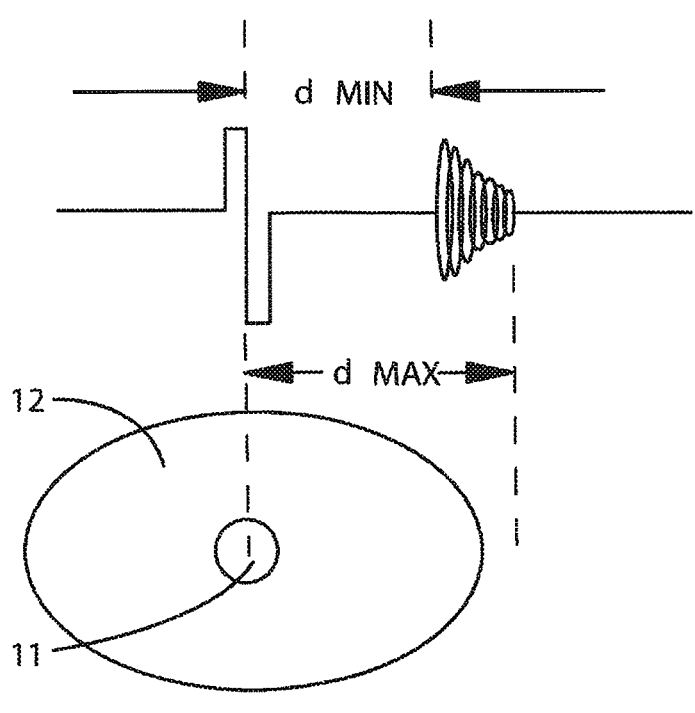
FIG. 11 is a schematic cross-sectional view of a non-circular bronchus, together with a graph depicting ultrasound pinging in the bronchus pursuant to the invention.

Apparatus according to one embodiment of the invention (FIG. 2) is advanced through the working channel of a bronchoscope 5. Alternatively an ultrasound catheter 10 can be advanced through a sheath or directly without any delivery instrument (FIG. 1) through an oral intubation device. The sheath or ultrasound catheter 10 generally may be in the form of an elongated tube having a proximal end, a distal end and a proximal-to-distal axis. As used in this disclosure with reference to elongated elements for insertion into the body, the term "distal" refers to the end which is inserted into the body first, i.e., the leading end during advancement of the element into the body, whereas the term "proximal" refers to the opposite end. The sheath or ultrasound catheter may be a steerable sheath or catheter. Thus, the sheath or catheter may include known elements such as one or more pull wires (not shown) extending between the proximal and distal ends of the sheath or catheter and connected to a steering control arranged so that actuation of the steering control by the operator flexes the distal end of the sheath or catheter in a direction transverse to the axis. The sheath or the ultrasound catheter 10 might be inserted into either the left bronchus $B_L$ or the right bronchus $B_R$ (FIG. 1) through an oral intubation device 202 as shown for a directly delivered ultrasound catheter 10 in FIG. 9B. One of the delivery techniques (as shown in FIG. 9A) might include an optical fiber 203 within the steerable sheath or within a central lumen of the ultrasound catheter. Once the main bifurcation has been passed, which can be seen through the optical fiber, one of the treatment areas has been reached and the optical fiber 203 is withdrawn from the sheath and replaced with the ultrasound treatment catheter 10 which is advanced as far as the optical fiber insertion length. Another delivery method relies on a length marking 204 (FIG. 9B) on the ultrasound catheter 10 or sheath. Once a certain length of the sheath/catheter shaft (determined pre procedure by CT, MRI or scoping) has been inserted, a treatment balloon 12 or distal sheath end has reached the target region as shown in FIG. 9B. Yet another delivery variant is to measure the degree of bending of the distal catheter portion though strain gages 206 (FIGS. 9C and 9D). The catheter 10 will be relatively straight as long as located in the trachea. A high degree of bending will be measured once the distal catheter portion is positioned distal to the main bifurcation MB in the right branch $B_R$ (or left branch $B_L$), as indicated in FIG. 9D. Another delivery method is to monitor the bronchial diameters through either inflation of balloon 12, FIG. 10B, or ultrasound measurement, as shown in FIG. 11. As soon as the diameter measures significantly less (about 50%) the main bifurcation has been passed, as indicated in FIG. 9E.

Figures 4A, 4B:
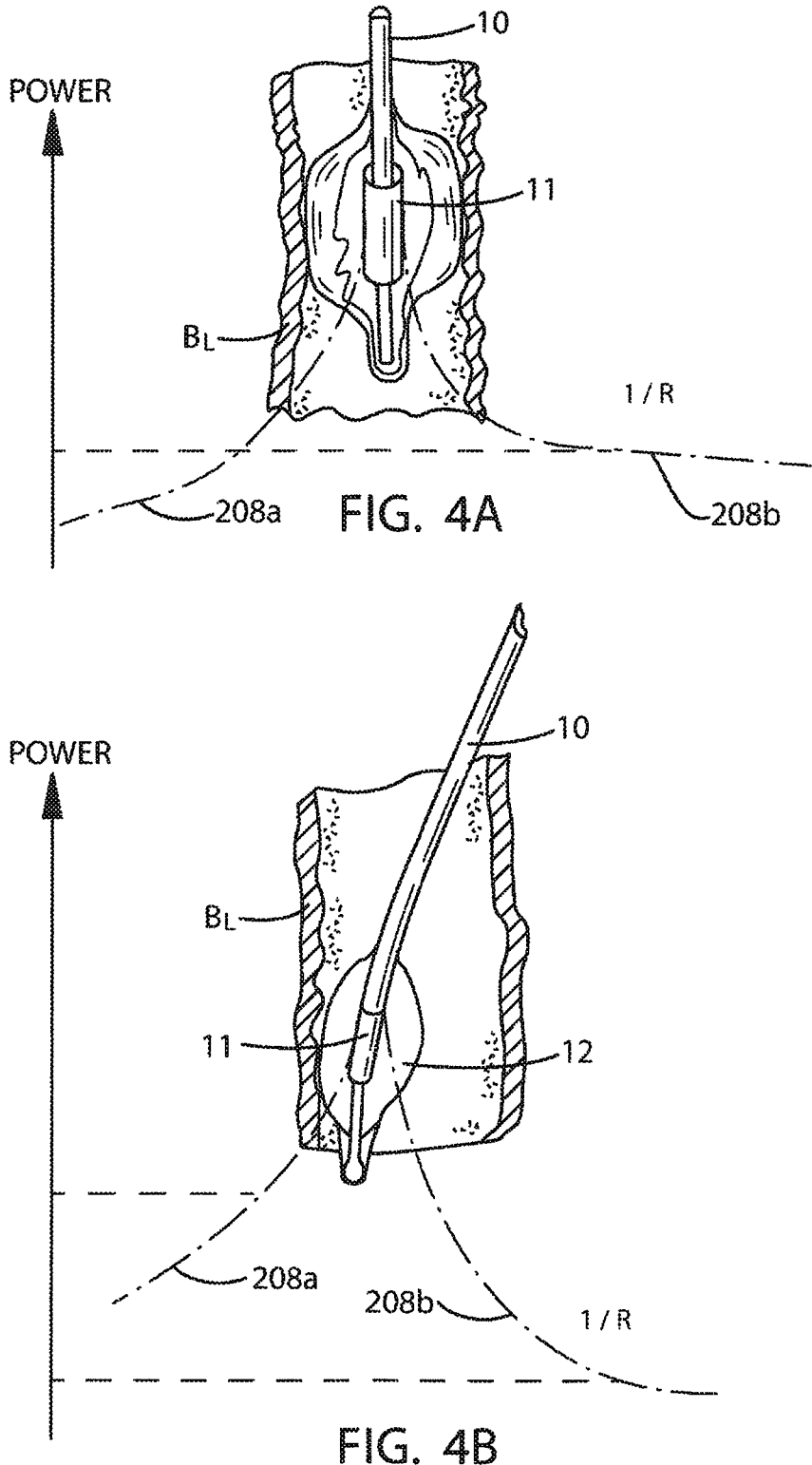
FIGS. 4A and 4B are a partial side elevational view of treatment apparatus and a partial longitudinal cross-sectional view of a bronchial tube, demonstrating the effects on power distribution of proper alignment in FIG. 4A in contrast with a non-centered, non-aligned ultrasound transducer in FIG. 4B

The apparatus includes the catheter 10 having a proximal end, a distal end and a proximal-to-distal axis which, in the condition depicted in FIG. 4A, is preferably coincident with the bronchial axis. Alignment with the bronchial axis will provide for a more homogeneous energy distribution through a cylindrical or annular treatment volume, as indicated in FIG. 4A by overlaid curves 208a and 208b of ultrasound power as a function of radial distance or displacement from a transducer 11 in the balloon 12 at the distal end of the catheter 10. In the case of misalignment the energy levels vary greatly from side to side, as indicated by power curves 210a and 210b in FIG. 4B. This skewing of the applied ultrasonic power distribution will cause wall injury on one side (210a) while the other side (210b) is ineffective in ablating nerves. Centering will cause the flatter portion of the 1/R curve to determine the energy distribution within the treatment volume as shown FIG. 4A.

Figures 2, 3:
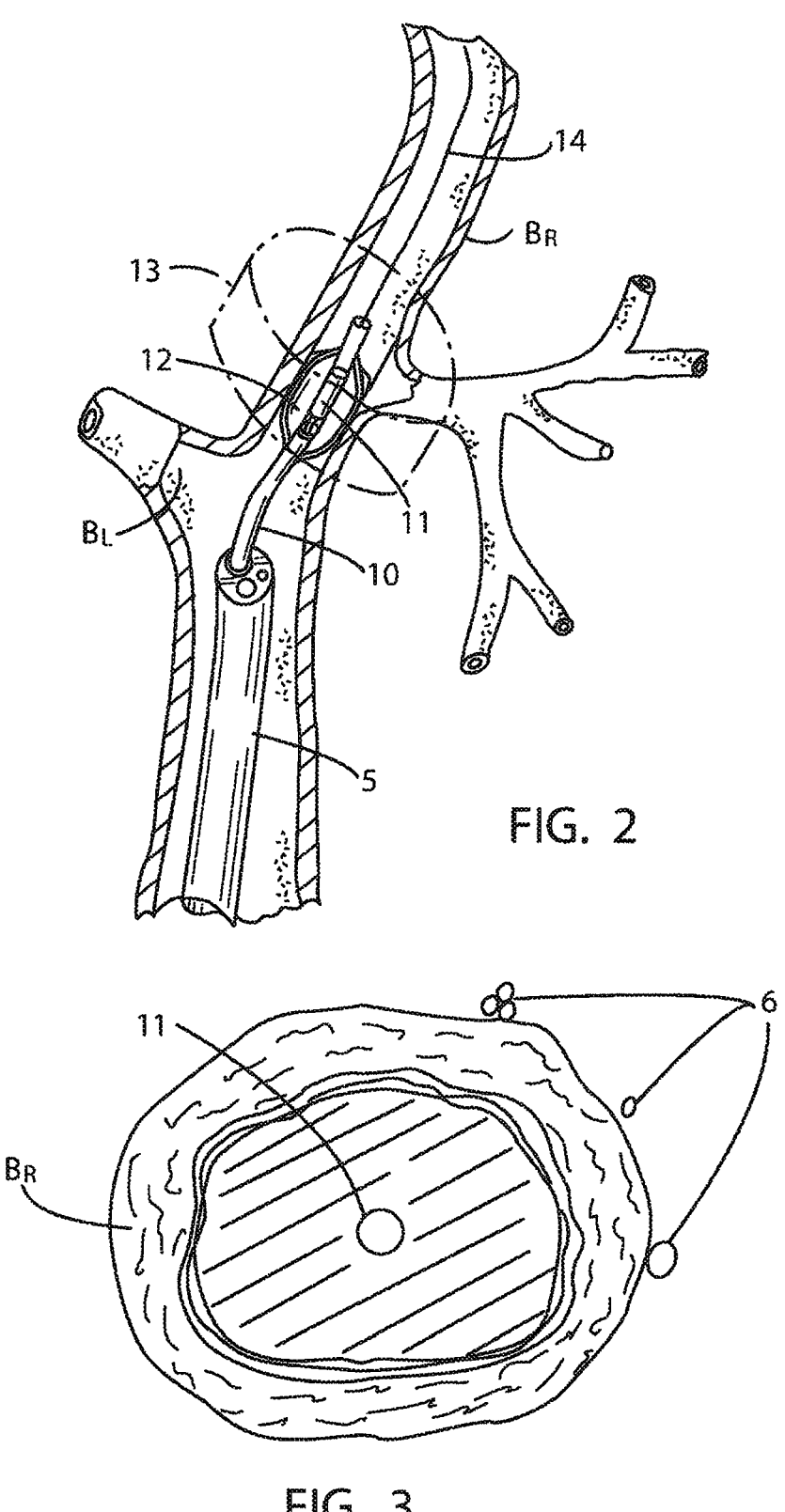
FIG. 2 is partially a side elevational view of a treatment catheter 10 advanced through a bronchoscope 5 into the right bronchial branch and a bronchial sectional view, diagrammatically depicting an ultrasound treatment volume 13.
FIG. 3 is a schematic transverse cross sectional view through a bronchial tube with an ultrasound transducer 11 in the center surrounded by cooling fluid in a compliant balloon.

Catheter 10 has compliant balloon 12 mounted at the distal end. In its inflated condition (FIGS. 2 and 3), balloon 12 engages the bronchial wall and therewith allows for ultrasound to be conducted from transducer 11 into bronchial wall and surrounding tissues 7 (FIG. 3).

Ultrasound transducer 11 (FIG. 3) is mounted adjacent the distal end of catheter 10 within balloon 12. Transducer 11, which is desirably formed from a ceramic piezoelectric material, is of a tubular shape and has an exterior emitting surface in the form of a cylindrical surface of revolution about the proximal-to-distal axis of the transducer 11. The transducer 11 typically has an axial length of approximately 2 and approximately 10 mm, and preferably about 6 mm. The outer diameter of the transducer 11 is approximately 1.5-3 mm in diameter, and preferably 2 mm. The transducer 11 also has conductive coatings (not shown) on its interior and exterior surfaces. Thus, the transducer may be physically mounted on a metallic support tube (not shown) which in turn is mounted to the catheter 10. The coatings are electrically connected to ground and signal wires. Wires 110 extend from the transducer 11 through a lumen in the catheter 10 to a connector 102 electrically coupled with the ultrasound system. The lumen (not designated) extends between the proximal end and the distal end of catheter 10, while the wires 110 extend from the transducer 11, through the lumen, to the proximal end of the catheter 10.

Transducer 11 is arranged so that ultrasonic energy generated in the transducer is emitted principally from the exterior or outer surface (not separately designated). Thus, the transducer may include features arranged to reflect ultrasonic energy directed toward the interior of the transducer so that the reflected energy, travelling outwardly, reinforces the ultrasonic vibrations at the exterior surface. For example, the support tube and transducer 11 may be configured so that the energy emitted from an interior surface of the transducer 11 is redirected outwardly to enhance the overall efficiency of the transducer. In this embodiment, the ultrasound energy generated by the transducer 11 is reflected at the interior mounting to reinforce ultrasound energy propagating from the transducer 11, thereby ensuring the ultrasound energy is directed outwardly from an external surface of the transducer 11.

Transducer 11 is also arranged to convert ultrasonic waves impinging on the exterior surface into electrical signals on wires 110. While A-mode signals integrated over the treatment volume cannot provide for spatial resolution like with an imaging transducer, a conclusion about the bronchial lumen can be made based on the magnitude of the amplitude and distance (time) of the volume-integrated A-mode signal. If the reflecting structure is not perfectly circular, the width of the reflected signal will be mathematically related, e.g., proportional, to the difference between a largest bronchial diameter dmax and a smallest diameter dmin (see FIG. 11). Stated another way, transducer 11 can act either as an ultrasonic emitter or an ultrasonic receiver. The receiving mode is of particular importance for an array type transducer as described in U.S. patent application Ser. No. 14/770,941, Publication No. 2016/0008636, because with an array type transducer 11 the received echoes can be electronically focused, using phased array processing, and high resolution images can be achieved.

The transducer 11 is designed to operate, for example, at a frequency of approximately 1 MHz to approximately a few tens of MHz, and typically at approximately 10 MHz. The actual frequency of the transducer 11 typically varies somewhat depending on manufacturing tolerances. The optimum actuation frequency of the transducer may be encoded in a machine-readable or human-readable element (not shown) such as a digital memory, bar code or the like affixed to the catheter. Alternatively, the readable element may encode a serial number or other information identifying the individual catheter, so that the optimum actuation frequency may be retrieved from a central database accessible through a communication link such as the internet.

Figure 1:
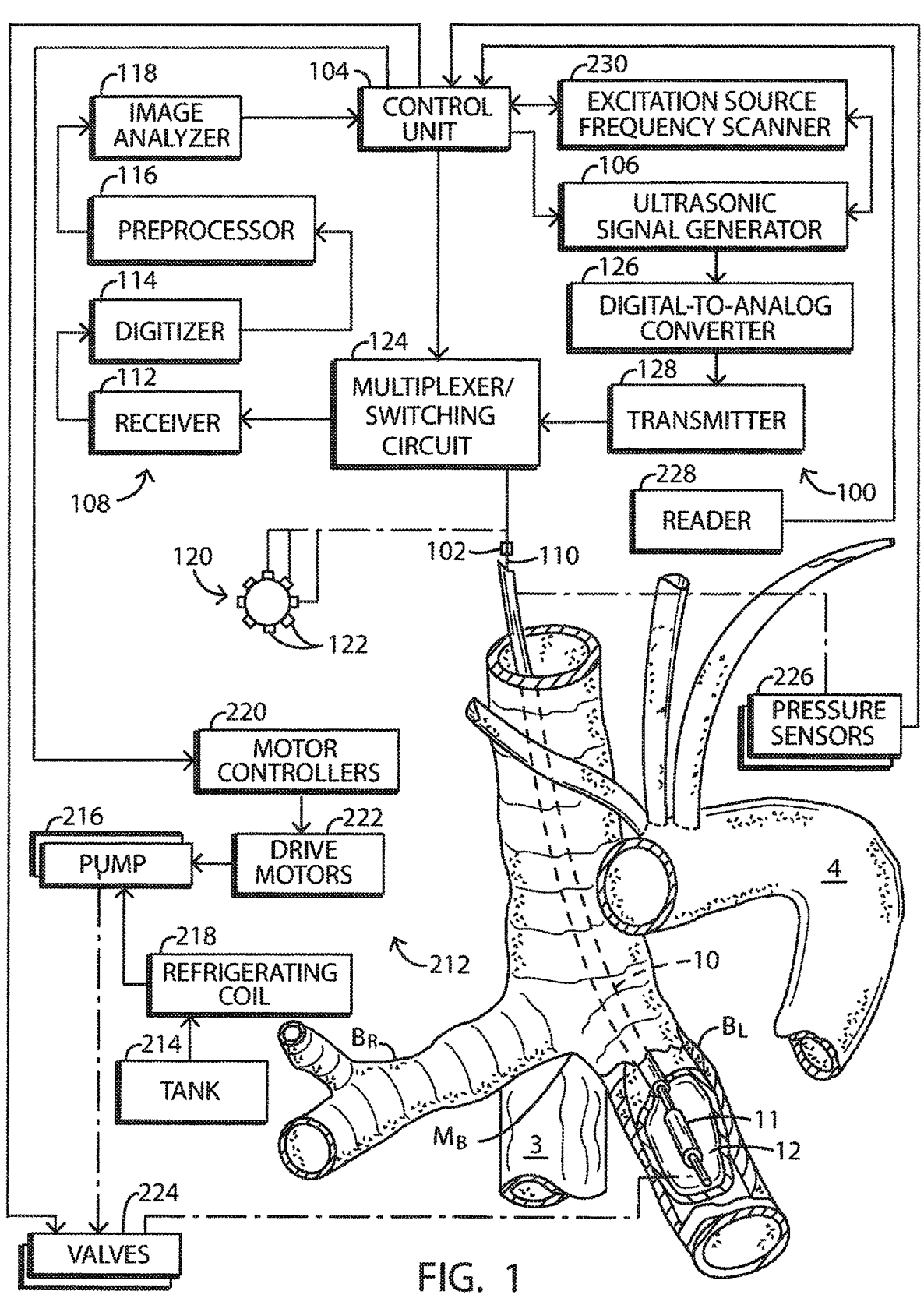
FIG. 1 is partially an anatomical view of typical main bronchial trunks $B_L$ and $B_R$ and associated structures and partially a block diagram of a system for treatment of pulmonary conditions, in accordance with the present invention.

An ultrasound system also referred to herein as an actuator, is releasably connected to catheter 10 and transducer 11 through a plug connector 102 (FIG. 1). A control unit 104 and an ultrasonic signal or waveform generator 106 are arranged to control the amplitude and timing of the electrical signals so as to control the power level and duration of the ultrasound-frequency signals emitted by transducer 11. An energization circuit 100 including control unit 104 and ultrasonic signal generator 106 also includes a detection subcircuit 108 arranged to detect electrical signals generated by transducer 11 and transmitted via wires 110 and communicate such signals to the control unit 104. More particularly, detection subcircuit 108 includes a receiver or echo signal extractor 112, a digitizer 114, an ultrasonic echo signal preprocessor 116, and an image analyzer 118 connected in series to one another. Ultrasonic signal generator 106 produces both therapeutic denervation signals and outgoing diagnostic imaging signals. As discussed hereinafter, the outgoing imaging signals and the returning echo signals may be transmitted and picked up by a circular array 120 of transducer elements 122 operating as a phased array. Transducer 11 may thus include an axial array of circular arrays 120 of transducer elements 122. A multiplexer or switching circuit 124 is operated by control unit 104 to switch to a receiving mode after imaging signals are emitted during a transmitting mode via a digital-to-analog converter 126 and a transmitter module 128.

As depicted in FIG. 1, a circulation device 212 is connected to lumens (not shown) within catheter 10 which in turn are connected to balloon 12. The circulation device 212 is arranged to circulate a liquid, preferably an aqueous liquid, through the catheter 10 to the transducer 11 in the balloon 12. The circulation device 212 may include elements such as a tank 214 for holding the circulating coolant, pumps 216, a refrigerating coil 218, or the like for providing a supply of liquid to the interior space of the balloon 12 at a controlled temperature, desirably at or below body temperature. The control unit 104 interfaces with the circulation device 212 to control the flow of fluid into and out of the balloon 12. For example, the control unit 104 may include motor control devices 220 linked to drive motors 222 associated with pumps 216 for controlling the speed of operation of the pumps. Such motor control devices 220 can be used, for example, where the pumps 216 are positive displacement pumps, such as peristaltic pumps. Alternatively or additionally, the control unit 104 may operate structures such as controllable valves 224 connected in the fluid circuit for varying resistance of the circuit to fluid flow.

Figure 10A:
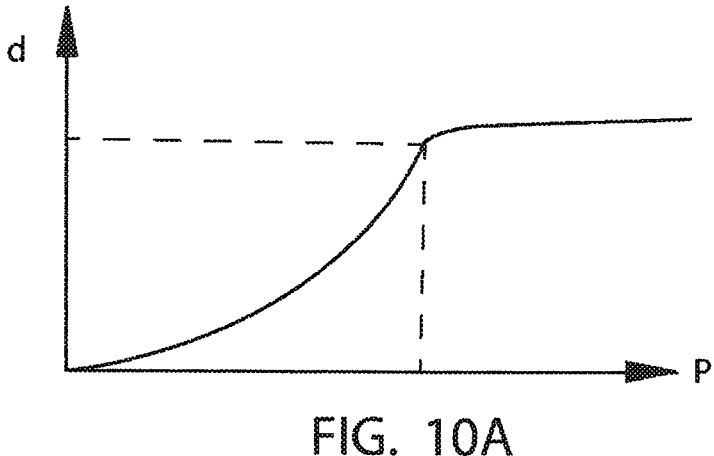
FIG. 10A is a graph relating to a pressure measurement technique for determination of bronchial diameter.

The ultrasound system may further include pressure sensors 226 (FIG. 1), to monitor the liquid flow through the catheter 10 and determine the bronchial diameter as shown in FIG. 10A by detecting the point of pressure increase without significant volume increase which corresponds with the balloon reaching full inflation inside the bronchus $B_L$ or $B_R$. The corresponding diameter can be determined through a look-up table, for instance, in a memory connected to control unit 104, where volume/pressure values are related to diameters. At least one pressure sensor 226 monitors the flow of the liquid to the distal end of catheter 10 to determine if there is a blockage while another pressure sensor 226 monitors leaks in the catheter 10. While the balloon 12 is in an inflated state, the pressure sensors 226 and 228 maintain a desired pressure in the balloon preferably so that the compliant balloon occludes the bronchus $B_L$ or $B_R$.

The ultrasound system 100 incorporates a reader 228 for reading a machine-readable element on catheter 10 and conveying the information from such element to the control unit or board 104. As discussed above, the machine-readable element on the catheter may include information such as the operating frequency and efficiency of the transducer 11 in a particular catheter 10, and the control unit 104 may use this information to set the appropriate frequency and power for exciting the transducer. Alternatively, the control unit 104 may be arranged to actuate an excitation source or frequency scanner 230 to measure the transducer operating frequency by energizing the transducer at a low power level while scanning the excitation frequency over a pre-determined range of frequencies for example 8.5 Mhz-10.5 Mhz, and monitoring the response of the transducer 11 to such excitation and to select the optimal operating frequency.

The ultrasonic system may be similar to that disclosed in U.S. patent application Ser. No. 14/770,941, Publication No. 2016/0008636, the disclosure of which is incorporated by reference herein.

A method according to an embodiment of the present invention is depicted in flowchart form in FIG. 7. After preparation of a human or non-human mammalian subject such as a patient (preparation of an tracheal access site), and connection of the catheter 10 to the ultrasound system, the ultrasound catheter 10 is inserted into the working channel of the bronchoscope (step 1206) after the bronchoscope has been advanced (steps 1202, 1204) to the desired treatment site under visual guidance through the bronchoscope camera or optical fiber. Alternatively, a steerable sheath, preferably with ultrasound imaging capability as described in U.S. patent application Ser. No. 14/770,941, Publication No. 2016/0008636, can be used as a delivery channel for the treatment catheter. In another embodiment the treatment catheter is equipped with a steering or deflection mechanism and can be advanced directly to the treatment site as shown in FIG. 1. If the catheter combines imaging and therapeutic capabilities as described in the U.S. patent application Ser. No. 14/770,941, Publication No. 2016/0008636, this delivery method enables the fastest procedure time and is easily tolerated by the patient. Yet another embodiment provides for a guide wire 14 (in FIG. 2) to be delivered through the working channel of the bronchoscope to the treatment site and the ultrasound treatment catheter to be advanced over the wire after the bronchoscope has been withdrawn. This technique will allow for very small, flexible bronchoscopes to be utilized.

Once the distal end of the catheter is in position within a main bronchial branch, pumps bring balloon 12 to an inflated condition (steps 1210 and 1212 in FIG. 7) as depicted in FIGS. 2 and 3. In this condition, the compliant balloon 12 engages the bronchial wall, and thus centers transducer 11 within the bronchial branch, with the axis of the transducer 11 approximately coaxial with the axis of the bronchial branch. This not only provides for a relatively homogeneous energy distribution circumferentially, but also keeps the very high energy levels close to the transducer located inside the cooling fluid where they are harmless, since ultrasound does not interact with fluid (see FIG. 4). If these peak energy levels were allowed to be located close to the bronchial wall (1), injury would result. These two situations are shown in FIGS. 4A and 4B where in FIG. 4A the ultrasound transducer 11 is properly centered and the energy is distributed without causing injury to the wall of the bronchus $B_L$ or $B_R$. Another advantage of proper centering is that the treatment volume coincides with the relatively flat portion of the 1/R curve, providing an almost constant power level throughout the treatment volume. In FIG. 4B the transducer 11 is not centered, resulting in uneven power distribution circumferentially. Also, the transducer 11 is positioned off axis (due to too small a balloon diameter) which exposes the bronchial wall to a peak power level which may cause wall injury.

During treatment (step 1214, FIG. 7), the circulation apparatus, including pump 216, coils 218, and valves 224 (FIG. 1), maintains a flow of cooled aqueous liquid into and out of balloon 12, so as to cool the transducer 11. The cooled balloon 12 also tends to cool the interior surface of the bronchus $B_L$, $B_R$. The liquid flowing within the balloon 12 may include a radiographic contrast agent to aid in visualization of the balloon and verification of proper placement under fluoroscopy.

Figures 5, 6:
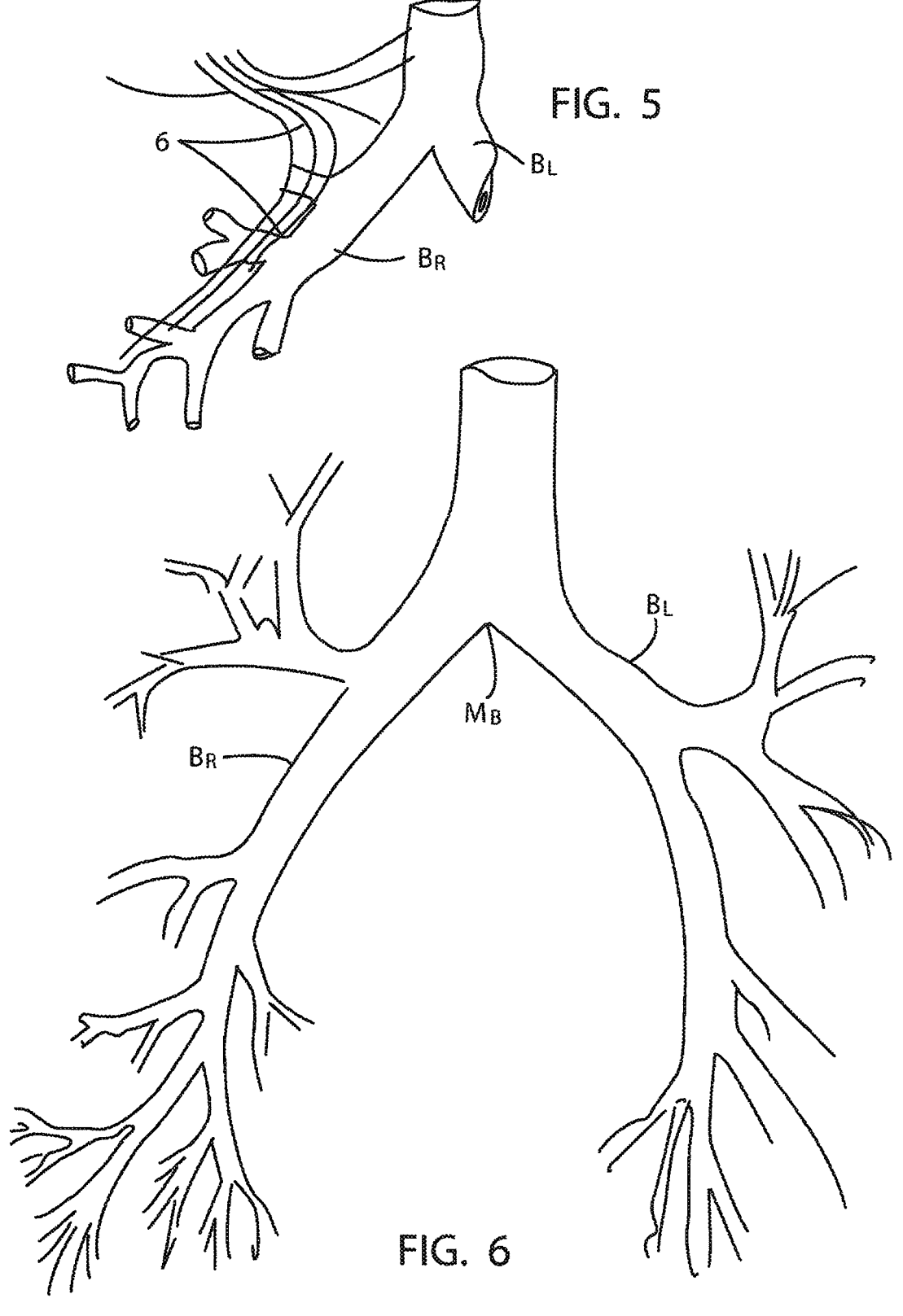
FIG. 5 is a side elevational view of a right bronchial branch showing adjacent nerves running alongside the bronchial tube.
FIG. 6 is a schematic elevational view showing a bronchial tree in its entirety.

In another embodiment, the ultrasound system uses transducer 11 to measure the size of the bronchus $B_L$, $B_R$ (see FIG. 6). The control unit 104 and ultrasound source or ultrasonic signal generator 106 actuate the transducer 11 to "ping" the bronchus with a low-power ultrasound pulse as shown in FIG. 11. The ultrasonic waves in this pulse are reflected by the bronchial wall onto transducer 11 as echoes. Transducer 11 converts the echoes to electrical echo-encoding signals. The ultrasound system, particularly control unit 104 (which typically takes the form of a programmed general-purpose computer or a hard wired processor), then determines the diameter of bronchus $B_L$ or $B_R$ by analyzing the echo signals. For example, the ultrasound system may determine the time delay between actuation of the transducer 11 to produce the "ping" and the return of echo signals. The width of the return signal represents the difference between diameter dmax and diameter dmin in case the bronchial section is not perfectly circular but oval shaped (see FIG. 11). The ultrasound system uses the measured bronchus size to set the acoustic power to be delivered by transducer 11 during application of therapeutic ultrasonic energy in later steps. For example, the control board or unit 104 may use a lookup table correlating a particular echo delay (and thus bronchial diameter) with a particular power level. Generally, the larger the diameter, the more power should be used. While the integrated A-mode signals over the treatment volume by a cylindrical uniform transducer cannot provide for spatial resolution, a conclusion about reflectors can be made based on the magnitude of the amplitude and distance (time) of the volume-integrated A-mode signal. In other words the presence of the balloon/tissue interface can be detected but cannot be differentiated circumferentially.

Figure 15A:
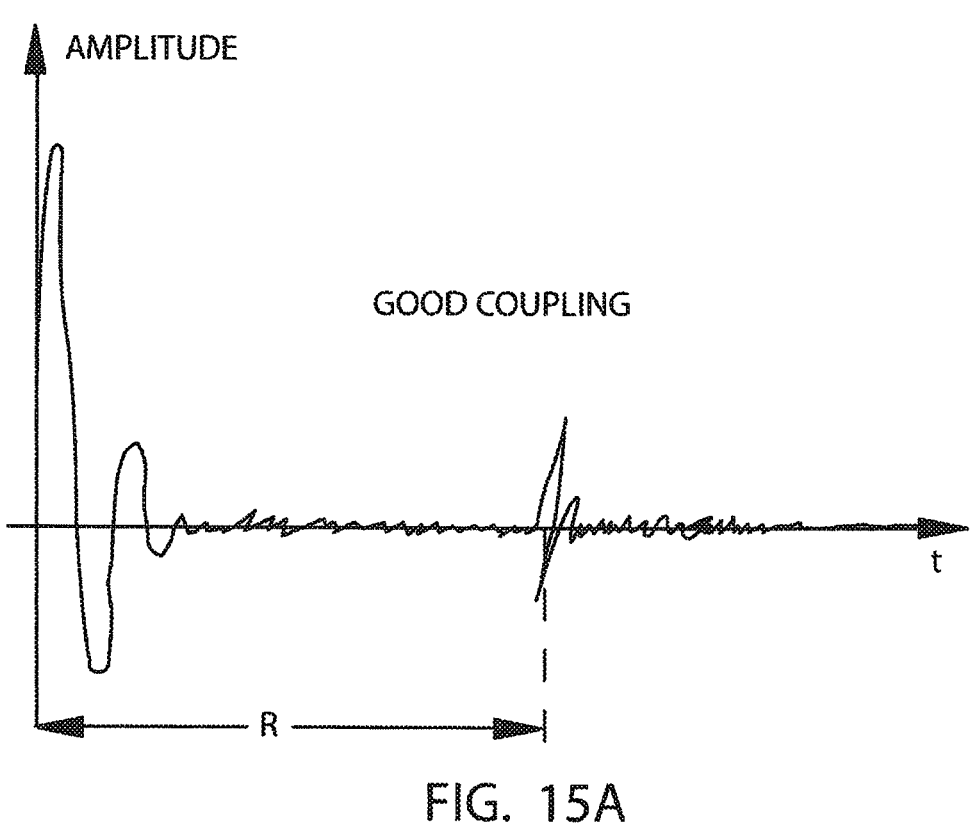
FIGS. 15A and 15B are graphs showing magnitudes of integrated A mode signals for complete (15A) and incomplete (15B) balloon-bronchus coupling.
Figure 15B:
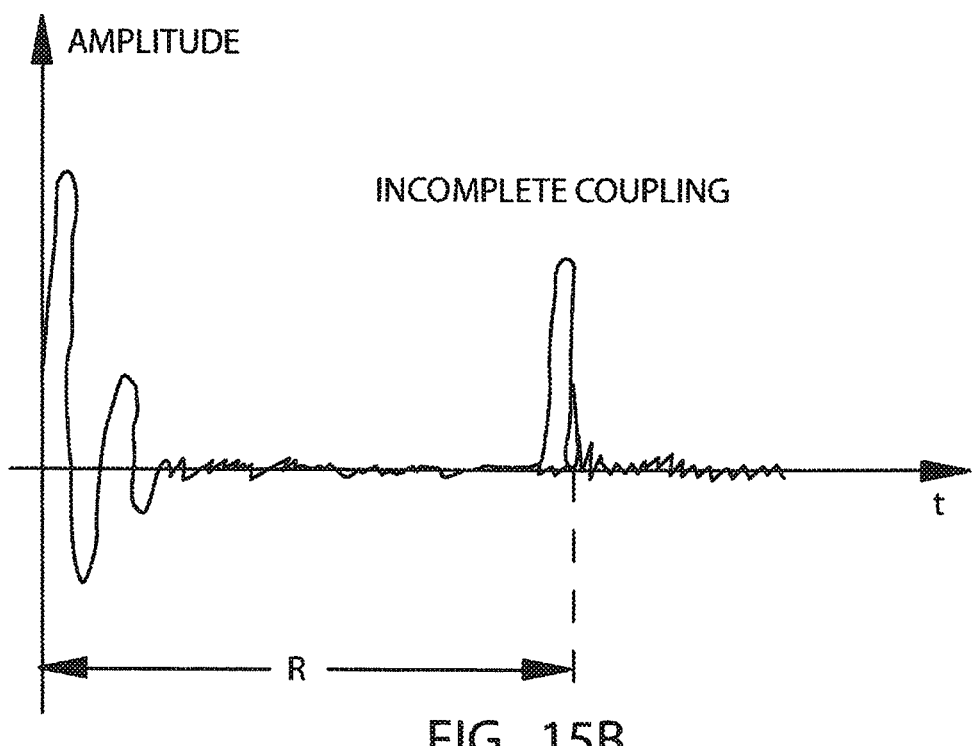

The volume integrated echo will also represent coupling of the balloon with the bronchial wall as shown in FIGS. 15A and 15B. If air is trapped the echo amplitude of the balloon/bronchus interface will be significantly larger as shown in FIG. 15B than in case of complete circumferential coupling as shown in FIG. 15A. While spatial resolution is not provided by this integrated A-mode signal, air pockets, i.e., trapped air, can be clearly detected by analyzing the amplitude of the integrated A-mode signal at the balloon/ bronchial interface or the corresponding time delay between transmit and receive echo as shown in FIGS. 15A and 15B. While the integrated A-mode signals over the treatment volume cannot provide for spatial resolution, a conclusion about trapped air can be made based on the magnitude of the amplitude and distance (time) of the integrated A-mode signal, see FIGS. 15A and 15B. In other words the presence of air at the balloon/tissue interface can be detected but the trapped air cannot be located circumferentially. If the balloon diameter is not adjusted properly to eliminate the trapped air, the energy will not be delivered completely circumferentially which will affect the efficacy of the procedure negatively.

Figures 14A, 14B:
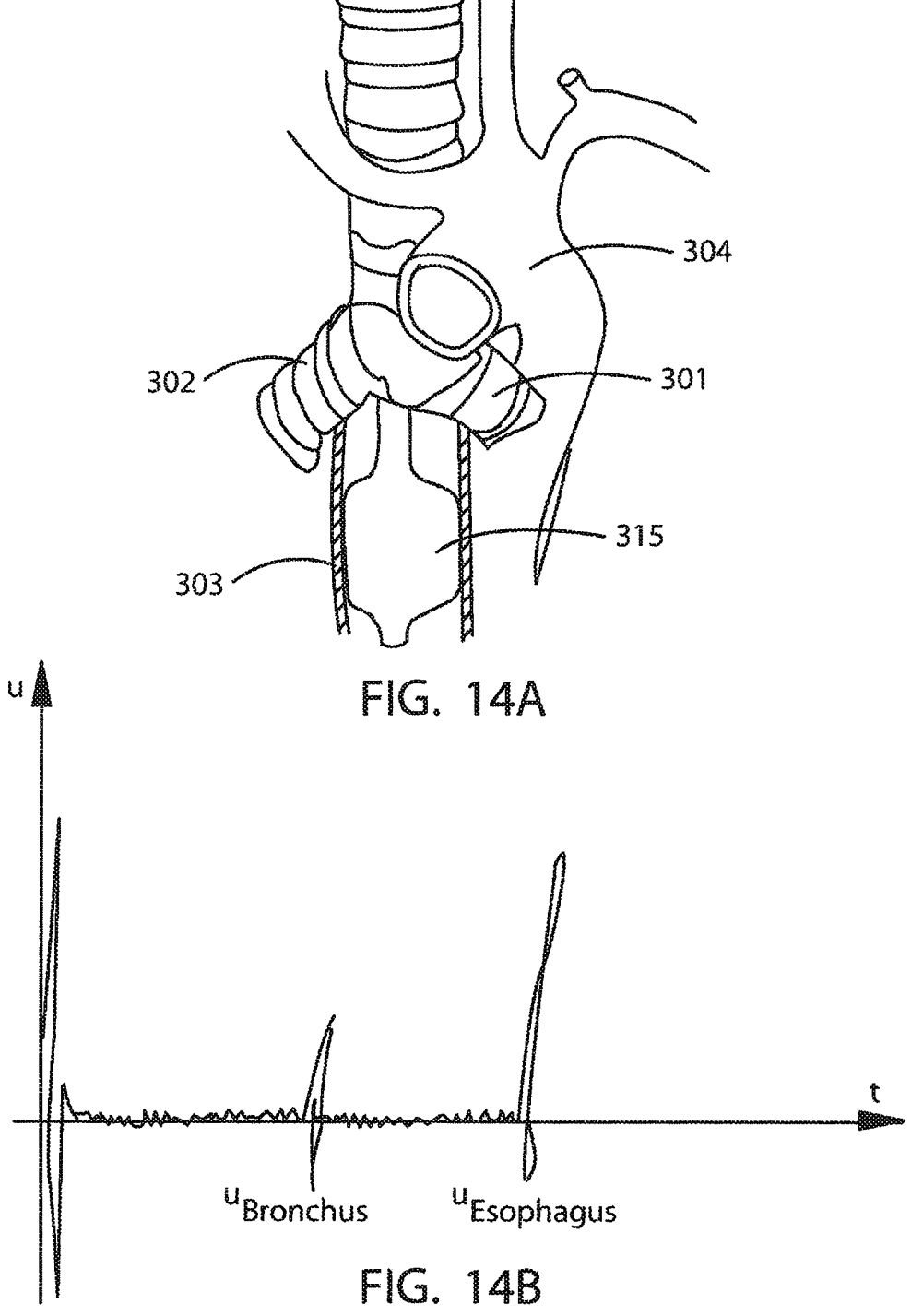
FIG. 14A is a diagram of a portion of the left (301) and right (302) main bronchus of a person's bronchial tree, showing the aorta (304) and an air filled balloon (315) positioned in the esophagus (303) to allow for esophageal distance determination.
FIG. 14B is a graph of intensity of an integrated ultrasound echo signal as a function of time after an ultrasound pulse emission in the configuration of FIG. 14A.

The volume integrated A-mode signal can also be analyzed to detect any air filled spaces in the treatment volume as shown in FIG. 14A, i.e., an air filled esophagus 303, due to an air filled balloon catheter 315 placed in the esophagus 303. The air filled balloon 315, proximate a distal end of the transducer-bearing catheter 10, registers as an artifact in the volume-integrated A-mode signal as shown in the graph of FIG. 14B. In order to avoid peri-esophageal nerve damage, the treatment catheter 10 will be advanced more distally in the bronchus $B_L$ or $B_R$ until the esophagus signal or artifact disappears or in other words the esophagus is located outside of the treatment volume. In extreme cases it might be necessary to advance the treatment volume distal to the first bronchial bifurcation so that 2 instead of 1 energy application are administered on that particular left or right side. As an additional safety measure, the air in the esophageal balloon 315 can be replaced with a circulating cooling fluid after distance detection to further reduce the chances of collateral esophageal damage. Otherwise, esophageal fistulae and/or peri-esophageal vagus nerve damage could result.

Figure 8A:
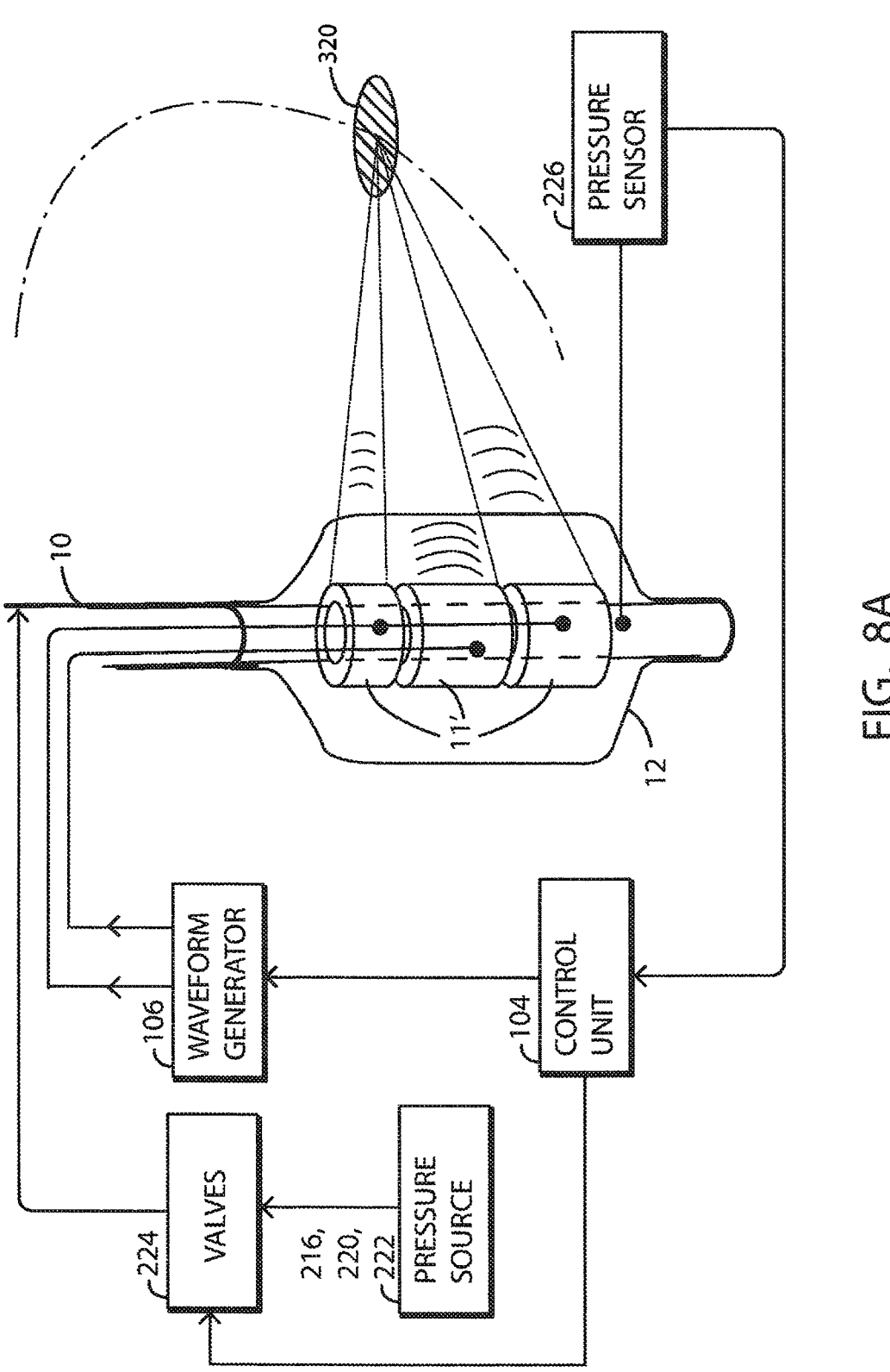
FIG. 8A-8C are diagrams illustrating different focusing mechanisms for an ultrasound catheter for use in a method in accordance with the present invention.
Figures 13A, 13B, 13C, 13D:
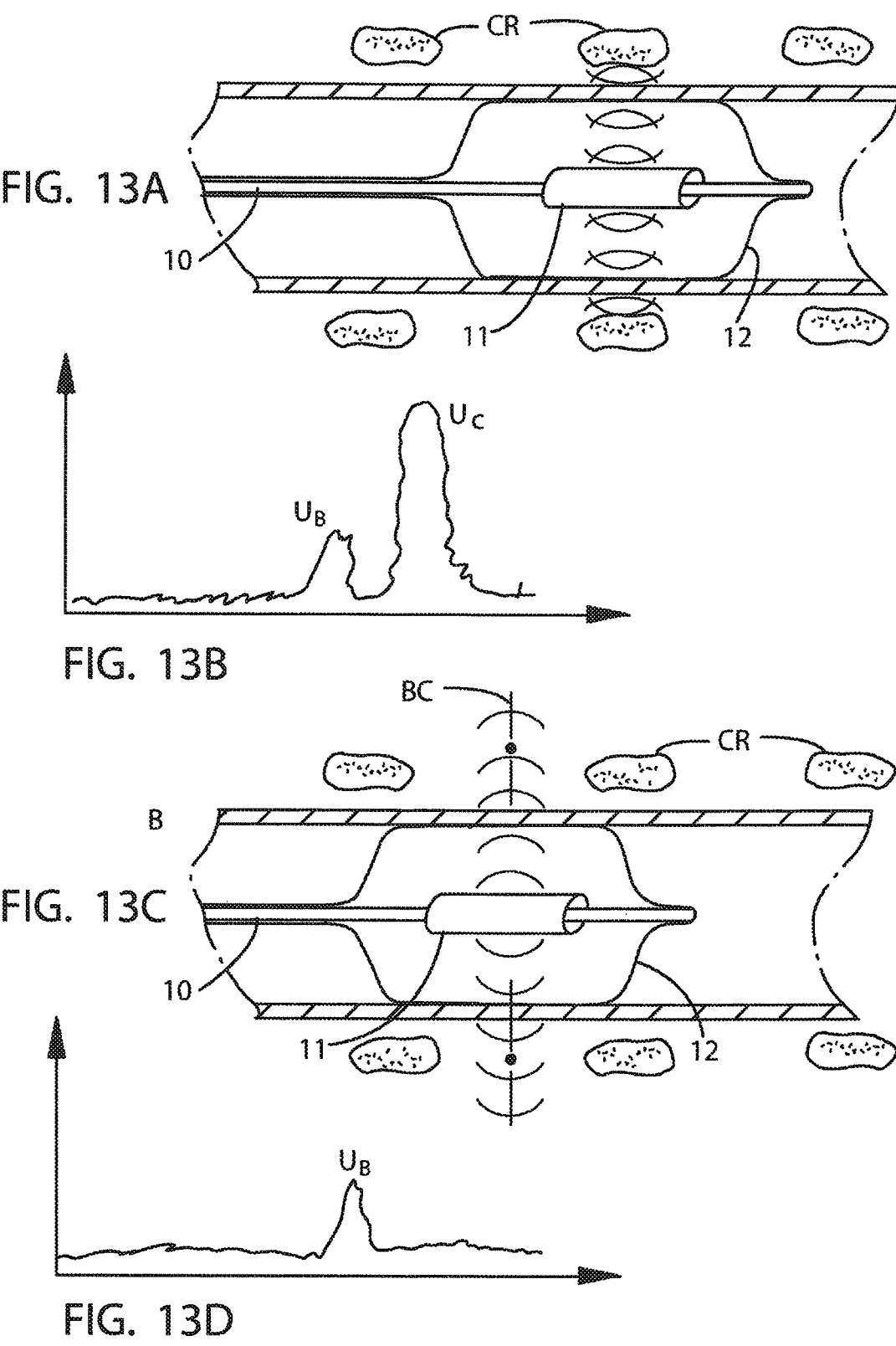
FIGS. 13A and 13C are cross sectional views of a main bronchus with an inserted ultrasound catheter with longitudinal position sensing and position optimization, showing the catheter and particularly an ultrasound transducer and balloon at different longitudinal positions in the bronchus, relative to cartilage rings thereof.
FIGS. 13B and 13D are graphs showing magnitudes of integrated A mode ultrasound echoes for the positions of the ultrasound catheter, transducer and balloon as shown in FIGS. 13A and 13C, respectively.

The volume integrated A-mode signal can also be analyzed to optimize positioning of the energy source or transducer 11 so that the portion of the ultrasound reflected by cartilage rings CR is minimized and the ultrasound treatment volume is positioned in a plane BC mainly between cartilage rings CR. FIG. 13A shows catheter 10, transducer 11 and balloon 12 positioned within a cartilage ring CR, that is, in a transverse plane of the cartilage ring. FIG. 13C depicts catheter 10, transducer 11 and balloon 12 positioned in a transverse plane BC between adjacent cartilage rings CR. Optimized positioning is obtained by analyzing the volume integrated A-mode signal and minimizing a circumferentially integrated cartilage echo Uc by moving the catheter 10, moving the transducer 11 inside the balloon 12 or by electronic selection of transducer sections as shown in FIG. 8A. For orientation, echo signal Uc will occur distally to a bronchial wall signal Ub. In other words rather than positioning ultrasound energy sources through mechanical seating mechanisms by forcing the ultrasound source into certain positions relative to cartilage rings, as described in U.S. Patent Application Publication No. 2016/0220851, the positioning is here controlled directly by detecting cartilage echoes and adjusting the longitudinal position of ultrasound source transducer 11 to optimally deliver the ultrasound energy in between cartilage rings CR. The complete catheter can be moved longitudinally until echo signal Uc is minimal or the transducer inside the balloon can be moved until echo signal Uc is minimal. In another embodiment transducer segments or groups thereof are activated until echo signal Uc is minimized and therewith an optimal positioning between cartilage rings CR has been obtained.

In any method generating and analyzing an integrated A-mode signal, the inserting of the ultrasound transducer 11 into the bronchial tree may be performed by any of the methods herein described, including (i) through a working channel of a bronchoscope under visual guidance, (ii) through a steerable sheath, (iii) with a steerable ultrasound catheter through an oral intubating device, (iv) under optical imaging guidance with an optical fiber inserted through the central lumen of the steerable ultrasound treatment catheter, and (v) without a sheath or bronchoscope, directly through an oral intubation device with a steerable ultrasound catheter with a distance scale marking for monitoring degree of insertion after conducting a CT, MRI procedure to ascertain distance along a bronchial tree to the bronchial section. The ultrasound transducer may be mounted to a distal end of a catheter, the inserting of the ultrasound transducer into the bronchial tree includes inserting the catheter so that the ultrasound transducer is placed at a desired operating position determined at least in part based on a bending radius of a distal catheter portion monitored via strain gages. Desired catheter position may be determined in part by monitoring the diameters of trachea and bifurcated bronchi, as described herein.

The physician initiates the treatment through a user interface (not illustrated). In the treatment, the ultrasonic system or actuator, and particularly the control board or unit 104 and ultrasonic signal source or generator 106, energizes transducer 11 to deliver therapeutically effective ultrasonic waves to an impact volume 13 (FIG. 2). The ultrasound energy transmitted by the transducer 11 propagates generally radially outwardly and away from the transducer 11 encompassing a full circle, or 360° of arc about the proximal-to-distal dimension or longitudinal axis of the transducer 11 and the axis of the bronchial section treated.

The selected operating frequency, focus-characteristic, placement, size, and the shape of the ultrasound transducer 11 allows the entire bronchial section and bronchial nerves to lie within the "focal field" of the transducer 11. As shown in FIG. 2, within this region an outwardly spreading, focused omni-directional (360°) cylindrical field of ultrasound waves is generated by the transducer 11. For a cylindrical transducer, the radial extent of the near field region, in which the beam can be focused, is defined by the expression $L^2/\lambda$, where L is the axial length of the transducer 11 and $\lambda$ is the wavelength of the ultrasound waves. At distances from the transducer 11 surface greater than $L^2/\lambda$, the beam begins to spread axially to a substantial extent. However, for distances less than $L^2/\lambda$, the beam does not spread axially to any substantial extent (FIG. 2) but can be focused. As used in this disclosure, the term "focused" refers to a beam, which increases in intensity in the direction of propagation of the beam away from the transducer 11. The impact volume 13 is generally cylindrical and coaxial with the bronchial section treated (FIG. 2). The impact volume extends from the balloon exterior or outer surface to an impact radius, where the intensity of the ultrasonic energy is too small to heat the tissue to the temperature range that will cause inactivation of nerves.

As discussed above, the length of the transducer 11 may vary between 2 mm and 10 mm, but is preferably 6 mm, to provide a wide aperture to enable focusing. The diameter of the transducer 11 may vary between 1.5 mm and 3.0 mm, and is preferably about 2.0 mm. The dosage is selected not only for its therapeutic effect, but also to allow the radius of the impact volume (focal zone) 13 to be preferably less than 5 mm from the balloon surface in order to encompass the bronchial section treated and adjacent bronchial nerves, all of which lie within an average radius of less than 5 mm from the balloon surface, without transmitting damaging ultrasound energy to collateral structures like esophagus 3, shown in FIG. 1 and 303 in FIG. 14A.

The power level desirably is selected so that throughout the impact volume, solid tissues are heated to about 42° C. or more for several seconds or more, but desirably all of the solid tissues, including the wall of the bronchus remain well below 65° C. Thus, throughout the impact region, the solid tissues (including all of the bronchial nerves) are brought to a temperature sufficient to inactivate nerve conduction but below that which causes rapid necrosis of the tissues.

Research shows that nerve inactivation occurs at much lower temperatures and much faster than tissue necrosis. See Bunch, Jared. T. et al. "Mechanisms of Phrenic Nerve Injury During Radiofrequency Ablation at the Pulmonary Vein Orifice, *Journal of Cardiovascular Electrophysiology*, Volume 16, Issue 12, pg. 1318-1325 (Dec. 8, 2005), incorporated by reference herein. Since, necrosis of tissue typically occurs at temperatures of 65° C. or higher for approximately 10 sec or longer while inactivation of nerves typically occurs when the nerves are at temperatures of 42° C. or higher for several seconds or longer, the dosage of the ultrasound energy is chosen to keep the temperature in the impact volume 13 between those temperatures for several seconds or longer. The dosage of ultrasonic energy desirably is also less than that required to cause substantial shrinkage of collagen in the impact volume. Operation of the transducer thus provides a therapeutic dosage, which inactivates nerves without causing damage to the bronchus $B_L$ or $B_R$. In addition, the circulation of cooled liquid through the balloon 12 containing the transducer 11 may also help reduce the heat being transferred from the transducer 11 to the inner layer of the bronchus. Hence, the transmitted therapeutic focused ultrasound energy does not damage the inner layer of the bronchus, providing a safe treatment.

In order to generate the therapeutic dosage of ultrasound energy, the acoustic power output of the transducer 11 typically is approximately 10 watts to approximately 100 watts, more typically approximately 20 to approximately 50 watts. The duration of power application typically is approximately 2 seconds to approximately a minute or more, more typically approximately 10 seconds to approximately 20 seconds. The optimum dosage used with a particular system to achieve the desired temperature levels may be determined by mathematical modeling or animal testing.

The impact volume 13 of the focused ultrasound energy encompasses the entire bronchial section treated and closely surrounding tissues, and hence encompasses all of the bronchial nerves surrounding the bronchus $B_L$ or $B_R$. Therefore, the placement in the bronchus $B_L$, $B_R$ of the transducer 11 may be indiscriminate in order to inactivate conduction of all the surrounding bronchial nerves 6 (see FIGS. 3 and 5) surrounding the bronchi in the subject. As used in this disclosure "indiscriminate" and "indiscriminately" mean without targeting, or locating on, any specific bronchial nerves. If the ablation is performed in the main bronchi, the ultrasound source position will be optimized to lay between cartilage rings as described above with reference to FIGS. 13A to 13D.

Optionally, the physician may then reposition the catheter 10 and transducer 11 along the bronchus $B_L$, $B_R$ and reinitiate the treatment to retransmit therapeutically effective focused ultrasound energy. This inactivates the bronchial nerves at an additional location along the length of the bronchial tree (FIG. 6), and thus provides a more reliable treatment. The repositioning and retransmission steps optionally can be performed multiple times. Next the physician moves the catheter 10 with the transducer 11 to the other main bronchus ($B_L$, $B_R$) and performs the entire treatment again for that bronchial side (see FIG. 6). After completion of the treatment, the catheter 10 is withdrawn from the subject's body.

Numerous variations and combinations of the features discussed above can be utilized. For example, the ultrasound system may control the transducer 11 to transmit ultrasound energy in a pulsed function during application of therapeutic ultrasonic energy. The pulsed function causes the ultrasound transducer 11 to emit the ultrasound energy at a duty cycle of, for example, 50%. Pulse modulation of the ultrasound energy is helpful in limiting the tissue temperature while increasing treatment times which will result in a more homogenous or even temperature distribution throughout the treatment volume. The pulsed therapeutic function can also be interleaved with a diagnostic imaging mode when the ultrasound transducer comprises an array of separately activatable transducer elements instead of a single unitary cylindrical transducer. This way diagnostic ultrasound imaging can be obtained essentially or quasi simultaneously with the therapeutic treatment, see U.S. patent application Ser. No. 14/770,941, Publication No. 2016/0008636.

In a further variant, the steps of measuring the bronchial size and adjusting the dose may be omitted. In this instance, the transducer is simply operated at a preset power level sufficient for the bronchial diameters of an average subject. In a further variant, the bronchial diameters can be measured by techniques other than actuation of transducer 11 as, for example, by radiographic imaging or magnetic resonance imaging, fiber optic imaging or use of a separate ultrasonic imaging catheter. In this instance, the data from the separate measurement can be used to set the dose.

In a further variant, the balloon 12 may be formed from a porous membrane or include holes, such that cooled liquid circulated within the balloon may escape or flow from the balloon 12 against the bronchial walls to improve acoustic contact.

Typically, catheter 10 is a disposable, single-use device. The catheter 10 or ultrasonic system may contain a safety device that inhibits the reuse of the catheter 10 after a single use. Such safety devices per se are known in the art.

In yet another variant, the catheter 10 itself may include a steering mechanism which allows the physician to directly steer the distal end of the catheter. In this case a bronchoscope or sheath may be omitted.

Another variation may be that an ultrasound energy emitter unit at the distal end of the catheter, which includes the ultrasound transducer, may be positioned in adjacent structures like the pulmonary artery or aorta (4 in FIG. 1 and 304 in FIG. 14A), and the ultrasound transducer may include reflective or blocking structures for selectively directing ultrasound energy from the transducer over only a limited range of radial directions toward the bronchial nerves. When this approach is utilized, the ultrasound energy is directed into a segment or beam propagating away from an exterior surface of the transducer, commonly known as a side firing transducer arrangement. For example, the ultrasound transducer may have a construction and be operated to emit as an ultrasound array and directed ultrasound energy under image guidance similarly as disclosed in U.S. patent application Ser. No. 14/770,941, Publication No. 2016/0008636, incorporated by reference herein. In this variation, the route by which the catheter is introduced into the body, and then positioned close to the bronchus, is varied from the bronchial approach discussed above.

FIG. 8A shows a multiple-element version of transducer 11 comprising a plurality of circular transducer elements 11' which can be activated individually or in combination. As discussed with reference to FIG. 1, each circular transducer element 11' may take the form of a circular array 120 of transducer elements 122 operating as a phased array. Transducer elements 11' may thus constitute an axial array of circular arrays of transducer elements. In response to signals from control unit 104, multiplexer or switching circuit 124 (FIG. 1) may switch between receiving and transmitting during an imaging mode of operation, so as to receive ultrasonic echoes or reflected waveforms after imaging signals are emitted via digital-to-analog converter 126 and transmitter module 128. During a therapeutic mode of operation, control unit 104 causes the phased array of transducer elements 11' (FIG. 8A) to focus ultrasound energy in an annular treatment zone 320 containing nerves to be deactivated. Control unit 104, again, may be a hard wired processor or a programmed general purpose computer or microprocessor. Also in response to signals from control unit 104, multiplexer or switching circuit 124 may switch between imaging and therapy modes.

Figures 8B, 8C:
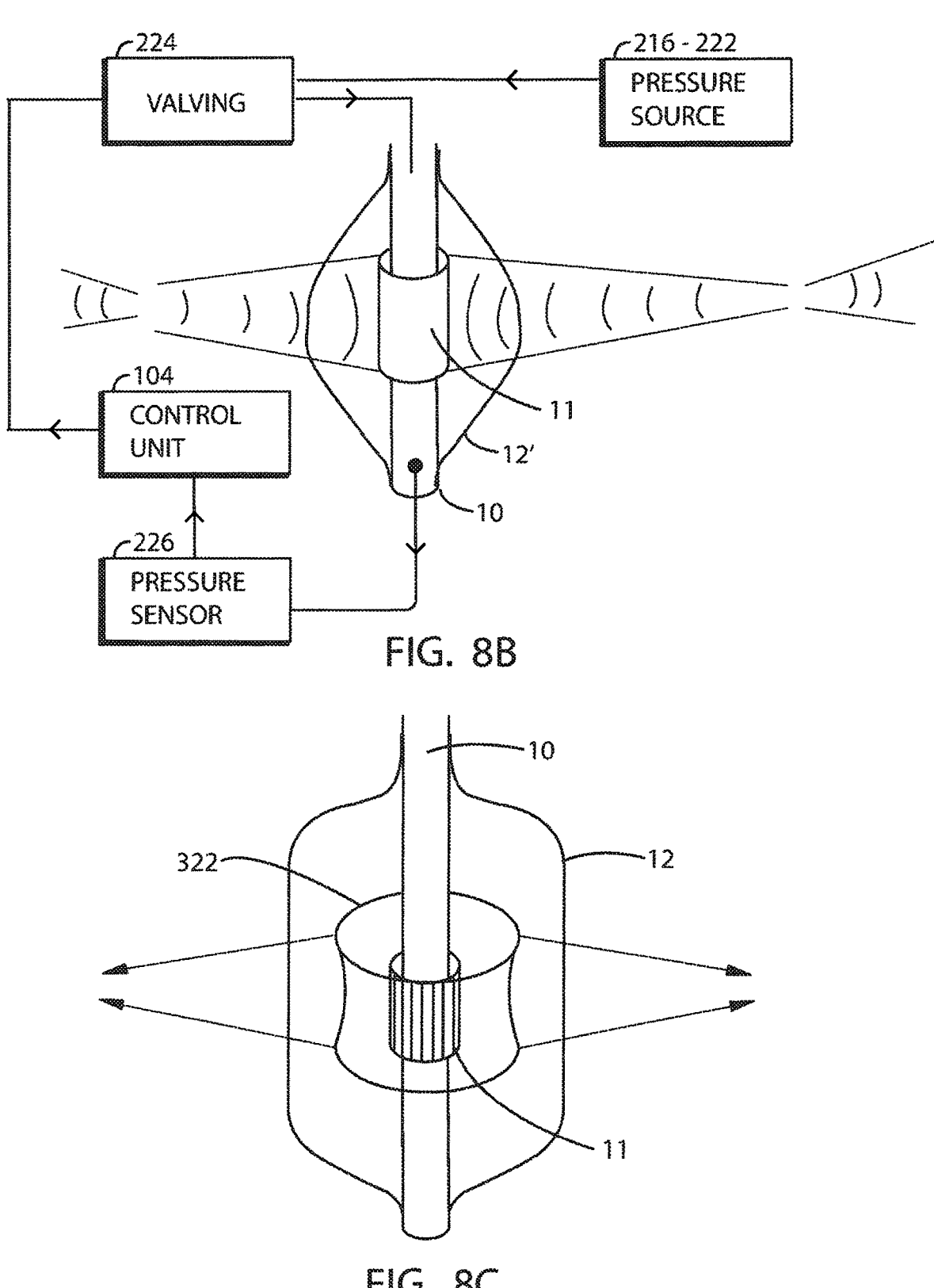

As shown in FIG. 8B, compliant balloon 12 is configured to function as fluid lens, whereby the diameter of the focal ring (see 320 in FIG. 8A) can be varied with balloon pressure by changing the shape of balloon 12 with pressure and therewith changing the lens effect. Of course the electronic focusing solution of FIG. 8A may be combined with the fluid lens balloon 12 of FIG. 8B. The focusing may be adjusted based on the bronchial diameter, corresponding to or matching the diameter of balloon 12, which can be calculated from balloon pressure or through ultrasound pinging, as described above with reference to FIGS. 10 and 11.

Figure 12:
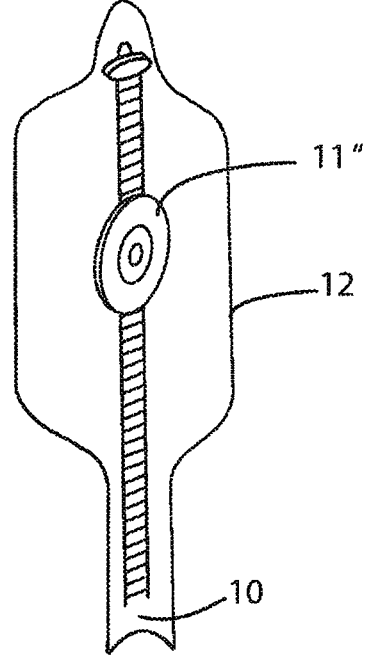
FIG. 12 is a schematic cross-sectional view of a rotary treatment and imaging catheter in accordance with the invention.

As depicted in FIG. 12, a rotating transducer 11" may be incorporated into a mechanical intravascular ultrasound (IVUS) system (e.g., of Boston Scientific, BSX). Therapeutic ultrasound pulses and/or full rotations may be interleaved with imaging pulses to generate quasi simultaneous imaging/therapy modes. The system (FIG. 1) circulating the coupling/cooling fluid might measure the fluid volume and or pressure and therewith determine the bronchial diameter (FIG. 10). Based on the measured bronchial diameter, the overall ultrasound power can be automatically optimized.

An additional application for the devices described above taking advantage of the energy dispersion characteristics (significant depth without undue near field damage; FIG. 4A) is lung tumor ablation. Once a lung tumor has been diagnosed with CT or MRI a guidewire is typically inserted under 3-dimensional guidance (i.e. Super Dimensions) in order to perform a biopsy. These systems combine 3D imaging with the localization of guidewires during bronchoscopy. However, treatment is typically performed later, in separate follow-up procedures. In the same biopsy procedure the guidewire may be used to advance the above-described ultrasound treatment catheter into the tumor. Depending on lesion volume, the ultrasound dose is calculated and one or more lesions are generated. Preferably, the ablation is performed under image guidance. In particular the annular array configuration of FIG. 12 provides image guidance of highest resolution which allows differentiation of tumor and normal tissues. In FIG. 12 a three element rotating annular array transducer 11" is shown. Another way to perform the tumor ablation, image guided, is to exchange treatment and imaging catheters over the guidewire. An IVUS imaging catheter may be advanced after withdrawal of the treatment catheter to monitor the tumor ablation progress and change back to the treatment catheter if the IVUS image shows non-ablated tumor regions.

An additional application for the devices described above is reducing negative effects of ARDS caused by COVID 19 by optimizing utilization of the remaining healthy lung capacity by preventing or reducing bronchial contraction and mucus secretion through denervation at the main bronchi.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for inactivating bronchial nerve conduction in a mammalian subject, comprising:

an elongated member supporting an ultrasound transducer adapted for insertion into a bronchial branch of a bronchial tree of the mammalian subject, the ultrasound transducer configured to transmit ultrasound energy in a first mode and in a second mode; and a control configured to control the transducer, the control adapted to a) control the ultrasound transducer to i) transmit ultrasound energy at a sub-therapeutic level for a diagnostic function in the first mode; ii) analyze circumferential A-mode ultrasound echoes from the transmitted ultrasound energy for the diagnostic function; and iii) process the A-mode ultrasound echoes to A-mode signals integrated over a treatment volume for the diagnostic function; and #) b) control the transducer to transmit ultrasound energy in a therapeutic function in the second mode so that the ultrasound energy is applied at a therapeutic level sufficient to inactivate conduction of bronchial nerves, the therapeutic level being below a level required for tissue necrosis.

2. The system of claim 1, wherein the control transmits ultrasound energy in the first mode to receive volume integrated ultrasound echoes to measure a diameter of the bronchial branch.

3. The system of claim 2, wherein the signals to measure the diameter is delivered in a low-power ultrasound pulse.

4. The system of claim 2, wherein the control is configured to adjust power settings of ultrasound based on the diameter of the bronchial branch.

5. The system of claim 1, wherein the system further comprises at least one pressure sensor to monitor liquid flow through the catheter and determine a diameter of the bronchial branch.

6. The system of claim 1, wherein the elongated member comprises a catheter having a balloon and the transducer is positioned within the balloon, the balloon containing a circulating cooling fluid.

7. The system of claim 1, wherein the elongated member comprises a catheter having a balloon and the transducer transmits energy in a 360 degree cylindrical pattern and the control detects whether circumferential contact of the balloon with the bronchial branch is complete or partial.

8. The system of claim 1, wherein the elongated member comprises a catheter having a balloon, wherein the control is configured to deliver ultrasound energy encompassing 360 degrees about a proximal to distal dimension of the transmitter.

9. The system of claim 1, wherein analysis of a return signal of a transmitted pulse in the first mode determines a circular or non-circular structure of the bronchial lumen.

10. The system of claim 1, wherein the control is configured to interleave pulses in the first mode and in the second mode to monitor progress in real time.

11. The system of claim 1, wherein the control unit is configured to determine position of cartilage rings based on ultrasound reflected in the first mode, and the elongated member is positioned to minimize a portion of the ultrasound reflection by cartilage rings and the control is configured to transmit ultrasound energy in the therapeutic mode to direct the ultrasound energy between the cartilage rings.

12. The system of claim 1, wherein the elongated member has a balloon and the transducer is movable inside the balloon for positioning between cartilage rings.

13. The system of claim 1, wherein the transducer comprises a plurality of transducer elements activatable individually or in combination.

14. The system of claim 1, wherein power adjustment is based on a determined diameter of a bronchial branch.

15. The system of claim 14, wherein the control transmits ultrasound energy in the first mode to generate a signal and process the A-mode ultrasound echoes to measure the diameter of the bronchial branch.

16. A system for inactivating bronchial nerve conduction in a mammalian subject, comprising:

an elongated member supporting an ultrasound transducer adapted for insertion into a bronchial branch of a bronchial tree of the mammalian subject, the ultrasound transducer configured to transmit ultrasound energy in a first mode and in a second mode; and a control configured to control the transducer, the control adapted to control the ultrasound transducer to i) transmit ultrasound energy at a sub-therapeutic level for a diagnostic function in the first mode; and ii) transmit ultrasound energy in a therapeutic function in the second mode so that the ultrasound energy is applied at a therapeutic level sufficient to inactivate conduction of bronchial nerves, the therapeutic level being below a level required for tissue necrosis, wherein the elongated member comprises a catheter having a balloon and the transducer is positioned within the balloon, and the system is configured to determine the diameter of the bronchial branch by detecting a pressure increase in relation to volume increase of the balloon.

17. The system of claim 16, wherein the diameter of the bronchial branch is determined through a look up table in a memory connected to the control, the look up table relating volume/pressure values with diameters.

18. The system of claim 16, wherein the elongated member has a balloon, a cooling fluid within the balloon, and the transducer within the balloon.

* * * * *